(12) United States Patent
Cuello et al.

(10) Patent No.: US 8,709,808 B2
(45) Date of Patent: Apr. 29, 2014

(54) ACCORDION BIOREACTOR

(75) Inventors: Joel L. Cuello, Tucson, AZ (US);
Joseph W. Ley, Denver, CO (US)

(73) Assignee: The Arizona Board of Regents, Tucson, AR (US)

( * ) Notice: Subject to any disclaimer, the term of this patent is extended or adjusted under 35 U.S.C. 154(b) by 421 days.

(21) Appl. No.: 12/949,678

(22) Filed: Nov. 18, 2010

(65) Prior Publication Data

US 2011/0287541 A1    Nov. 24, 2011

Related U.S. Application Data

(60) Provisional application No. 61/281,552, filed on Nov. 19, 2009.

(51) Int. Cl.
*C12M 1/00* (2006.01)
*C12M 3/00* (2006.01)
*C12N 1/12* (2006.01)

(52) U.S. Cl.
CPC .............. *C12M 21/02* (2013.01); *C12M 23/26* (2013.01); *C12M 23/34* (2013.01); *C12M 23/44* (2013.01); *C12M 41/08* (2013.01); *C12N 1/12* (2013.01)
USPC ...................... 435/383; 435/292.1; 435/257.1

(58) Field of Classification Search
USPC .......................... 435/252.1, 257.1, 292.1, 383
See application file for complete search history.

(56) References Cited

U.S. PATENT DOCUMENTS

| 4,952,511 A | 8/1990 | Radmer |
| 5,162,051 A | 11/1992 | Hoeksema |
| 5,443,985 A | 8/1995 | Lu et al. |
| 6,509,188 B1 | 1/2003 | Trösch et al. |
| 2008/0160591 A1* | 7/2008 | Willson et al. ................ 435/132 |

(Continued)

FOREIGN PATENT DOCUMENTS

| WO | WO 95/06111 | 3/1995 |
| WO | WO 2007/098150 | 8/2007 |

(Continued)

OTHER PUBLICATIONS

"Algae Photobioreactor in UA: UA Researcher Predicts Algae Biofuel at the Pump in 5 Years," http://home.ateneoinnovation.org/index.php?option=com_content&view=article&id=449:algae-photobioreactor-in-ua&catid=1:latest-news&Itemid=50, Five pages, Feb. 22, 2010.

(Continued)

*Primary Examiner* — Michael Hobbs
*Assistant Examiner* — Liban Hassan
(74) *Attorney, Agent, or Firm* — Klarquist Sparkman, LLP

(57) ABSTRACT

Disclosed herein are bioreactors including a first sheet and a second sheet, wherein the second sheet is disposed adjacent to the first sheet, and the first and second sheets are sealed along a first longitudinal edge, a second longitudinal edge, a first horizontal edge, a second horizontal edge, and at least one intermediate horizontal seal, thereby forming at least two chambers for holding fluid in series along a vertical axis, wherein each of the two or more chambers is oriented at an angle relative to the vertical axis, and at least one of the chambers is oriented at an angle greater than 0°, and wherein there is at least one opening in each of the first horizontal edge, the second horizontal edge, and intermediate horizontal seal(s); Also disclosed are methods of culturing cells including circulating a suspension of cells in a disclosed bioreactor.

22 Claims, 11 Drawing Sheets

(56) References Cited

U.S. PATENT DOCUMENTS

2008/0274494 A1* 11/2008 Kertz .............................. 435/29
2009/0053762 A1    2/2009 Shaaltiel

FOREIGN PATENT DOCUMENTS

| WO | WO 2009/040383 | 4/2009 |
| WO | WO 2009/069967 | 6/2009 |
| WO | WO 2009/090549 | 7/2009 |
| WO | WO 2009/155032 | 12/2009 |
| WO | WO 2010/076795 | 7/2010 |

OTHER PUBLICATIONS

Xu et al., "Microalgal bioreactors: Challenges and opportunities," *Eng. Life Sci.*, vol. 9, No. 3, pp. 178-189, 2009.

* cited by examiner

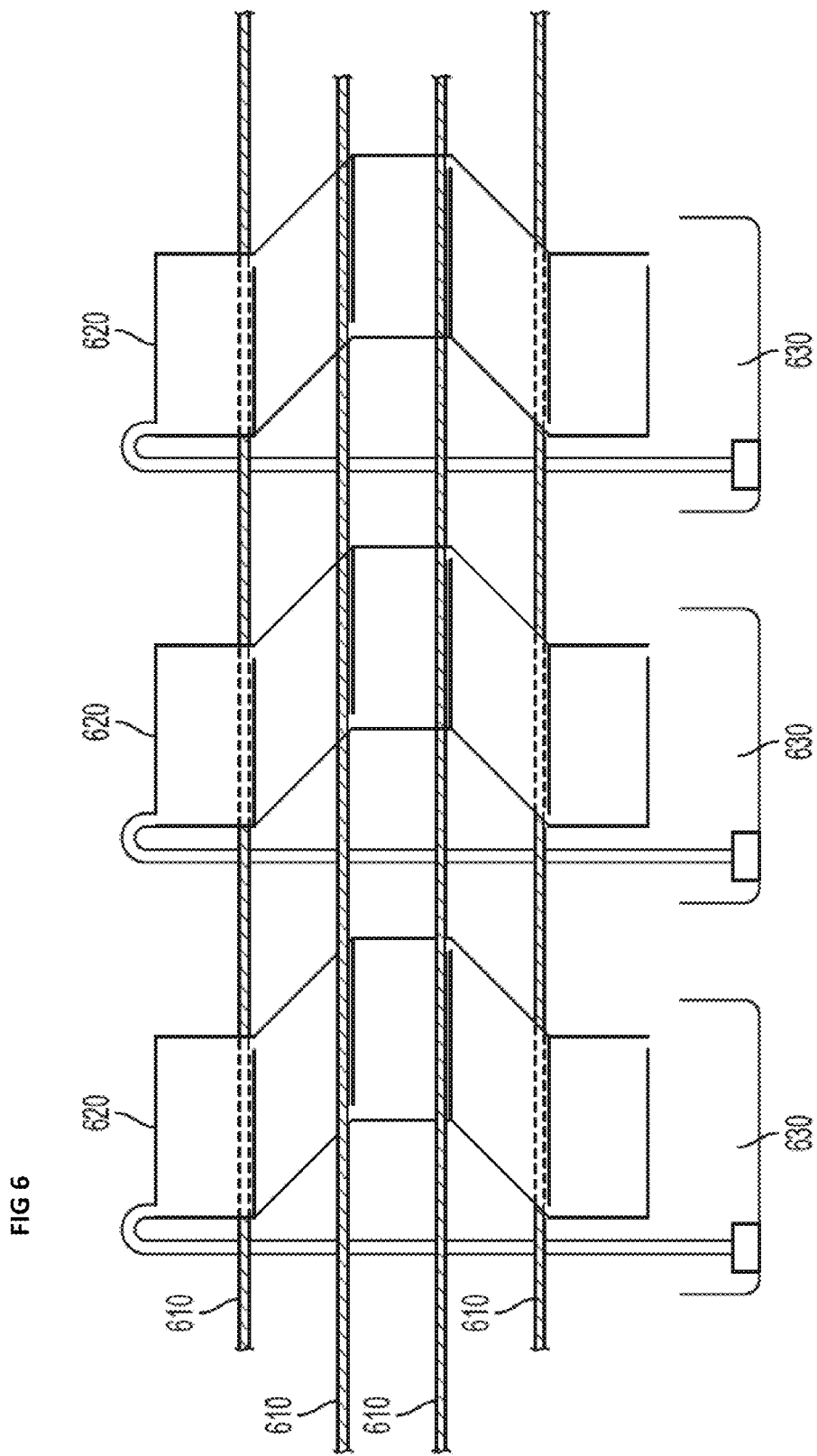

FIG 8
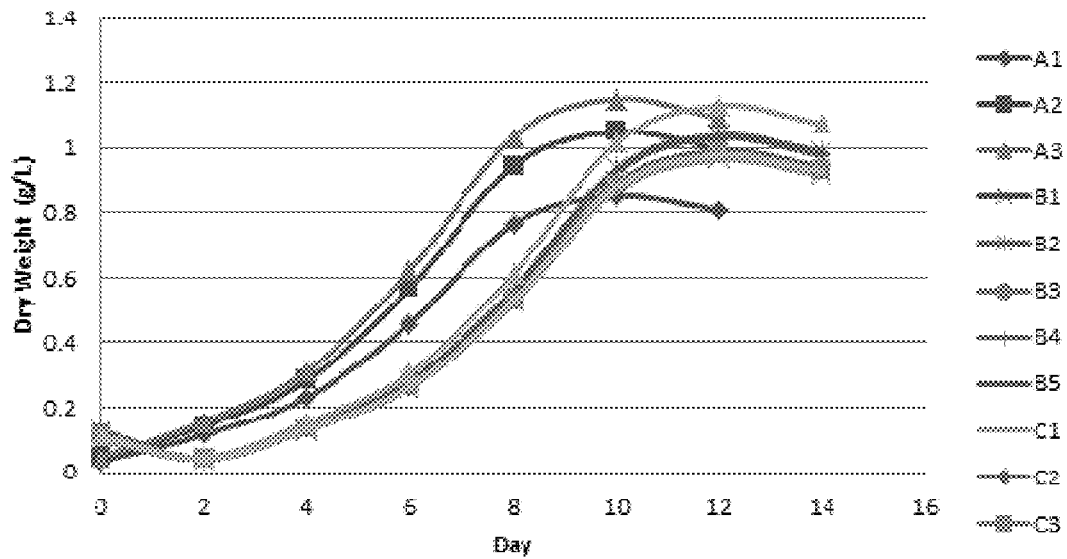
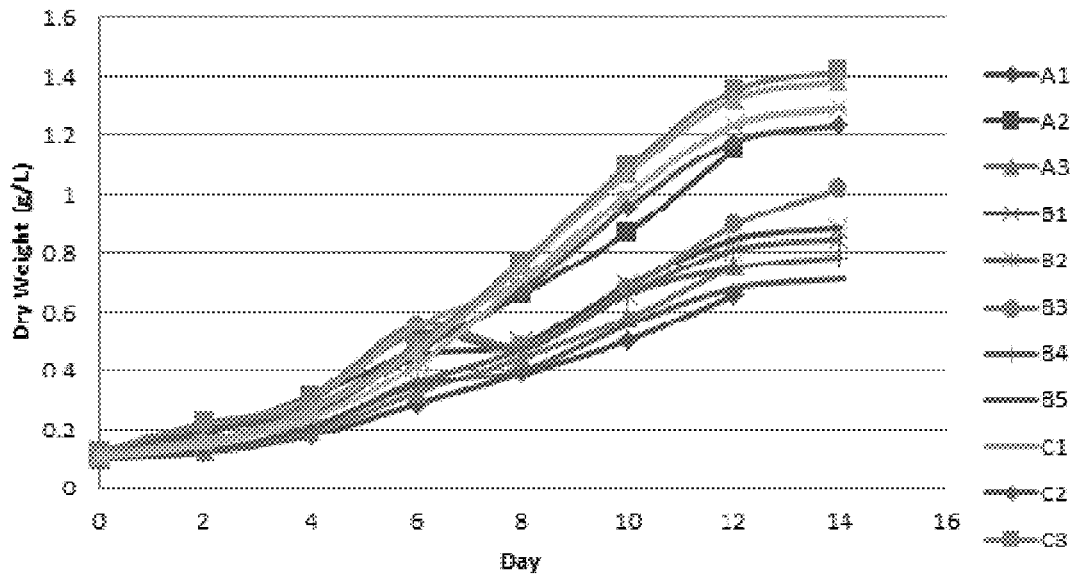

ACCORDION BIOREACTOR

CROSS REFERENCE TO RELATED APPLICATIONS

This claims the benefit of U.S. Provisional Application No. 61/281,552, filed Nov. 19, 2009, which is incorporated herein by reference in its entirety.

FIELD

This disclosure relates to bioreactors, particularly photobioreactors, for example for algal culture.

PARTIES TO JOINT RESEARCH AGREEMENT

This application describes and claims certain subject matter that was developed under a written joint research agreement between The Arizona Board of Regents on behalf of the University of Arizona and Biopharmia AS.

BACKGROUND

Development of alternatives to fossil fuels is a major scientific and economic concern. Such fuels have the potential to provide a reliable and sustainable source of energy, while at the same time greatly limiting release of carbon dioxide to the environment from the burning of fossil fuels. The term biofuel refers to a fuel that is biological in origin and is in some way derived from the biomass of a plant or other organic matter. Biofuels can be in solid, liquid, or gaseous form and can be used in a variety of ways, ranging from the combustion of wood for heating to the use of bioethanol and biodiesel as a transportation fuel. When considering liquid transportation fuels, multiple feedstocks have been studied and developed. In particular, ethanol derived from corn stands out as the most mature and widely commercialized option. Recently, however, the many drawbacks of using corn as a biofuel feedstock have become apparent. Any biofuel feedstock must not compete with food supplies in order to be considered a viable large scale alternative fuel. Biofuels that do not compete or interfere with food production are attractive because the end product is a fuel that is near identical to petroleum based fuels and will not require any substantial reworking of the current transportation fuel infrastructure. Vehicles based on electric power or fuel cells would require entirely new vehicle designs and significantly modified fuel or power distribution systems. When considering biofuel feedstocks for development it is also important to consider the water consumption and land area that will be required to produce the feedstock.

Microalgae have recently emerged as a promising biofuel feedstock because they meet many of the criteria stated above. The lipid portion of the microalgae biomass can be converted into a form of diesel which is nearly identical to petroleum diesel. In addition, production of algae does not interfere with world food production in any significant way.

Two general approaches are currently utilized for algae culture. Open systems (such as open ponds or raceways) are highly economical to build and operate; however, they have significant disadvantages, such as contamination risk, fluctuations in environmental conditions, and lower and less reliable productivity. Closed systems (such as photobioreactors) have the advantages of control of environmental conditions, low risk of contamination, and higher productivity and reliability than open systems. The primary disadvantage of closed systems is their relatively high cost for construction and operation.

SUMMARY

Disclosed herein are bioreactors (such as photobioreactors, for example for algal culture) that have the advantages of closed systems and also are relatively low cost to construct and operate. The disclosed bioreactors also are modular, allowing for simple scale-up, and can be easily adjusted (for example, automatically) for optimizing culture conditions, such as incident light exposure.

In one embodiment, the disclosed bioreactor includes a first sheet and a second sheet (one or both of which is substantially transparent to light), wherein the second sheet is disposed adjacent to the first sheet, and the first and second sheets are sealed along a first longitudinal edge, a second longitudinal edge, a first horizontal edge, a second horizontal edge, and at least one intermediate horizontal seal between the first horizontal edge and the second horizontal edge, thereby forming at least two chambers for holding fluid in series along a vertical axis, wherein each of the two or more chambers is oriented at an angle relative to the vertical axis, wherein the angle is about 0° to about 90° and at least one of the chambers is oriented at an angle greater than 0°, and wherein there is at least one opening in each of the first horizontal edge, the second horizontal edge, and intermediate horizontal seal(s); a support structure comprising at least one horizontal support, wherein the horizontal support is located at or near the position of the intermediate horizontal seal; a reservoir below the second horizontal edge of the first and second sheets; and means for pumping fluid from the reservoir to the first horizontal edge of the first and second sheets. In some examples, the angle greater than 0° is about 30° to about 75°.

In some examples, at least one of the first and second sheets is transparent. In further examples, the first and second sheets are made of a flexible material (such as polyethylene) or a rigid material (such as polycarbonate).

In some embodiments, the bioreactor includes two or more intermediate horizontal seals (such as 2-100 intermediate horizontal seals). In particular examples, the one or more intermediate horizontal seals are approximately horizontal relative to the floor or ground, are upwardly angled relative to the floor or ground, or are downwardly angled relative to the floor or ground. In some examples, the bioreactor includes multiple horizontal intermediate seals, which can include any combination of horizontal, upwardly angled, or downwardly angled seals (that is, the intermediate horizontal seals do not all need to be parallel to each other or parallel to the floor or ground).

The disclosure includes embodiments including a modular arrangement of the disclosed bioreactors, such as multiple vertical series of chambers arranged adjacent to one another. In some examples, the modular arrangement includes a common structural support (such as at least one horizontal support) that supports multiple bioreactors. In other examples, the modular arrangement includes a common reservoir for multiple vertical series of chambers.

The disclosure also includes methods of culturing cells including circulating a suspension of cells in a disclosed bioreactor. In some examples, the cells include microalgae, macroalgae, bacteria, fungi, insect cells, plant cells, animal cells (such as mammalian cells), or plant or animal tissue or organs. In particular examples, the method includes exposing the culture in the bioreactor to a light source (such as sunlight or an artificial light source).

The foregoing and other features of the disclosure will become more apparent from the following detailed description, which proceeds with reference to the accompanying figures.

BRIEF DESCRIPTION OF THE DRAWINGS

FIG. 5A is a diagram showing a serpentine layout. FIG. 5B is a diagram showing alternating middle and edge position openings. FIG. 5C is a diagram showing upwardly angled intermediate horizontal seals. FIG. 5D is a diagram showing downwardly angled intermediate horizontal seals. Arrows indicate the general direction of fluid flow.

FIG. 6 is an elevation view of an exemplary modular bioreactor set-up.

FIG. 8 is a pair of graphs showing growth curves of algae grown under various ACCORDION bioreactor conditions. The conditions are set forth in Table 4.

DETAILED DESCRIPTION

Figure 1:
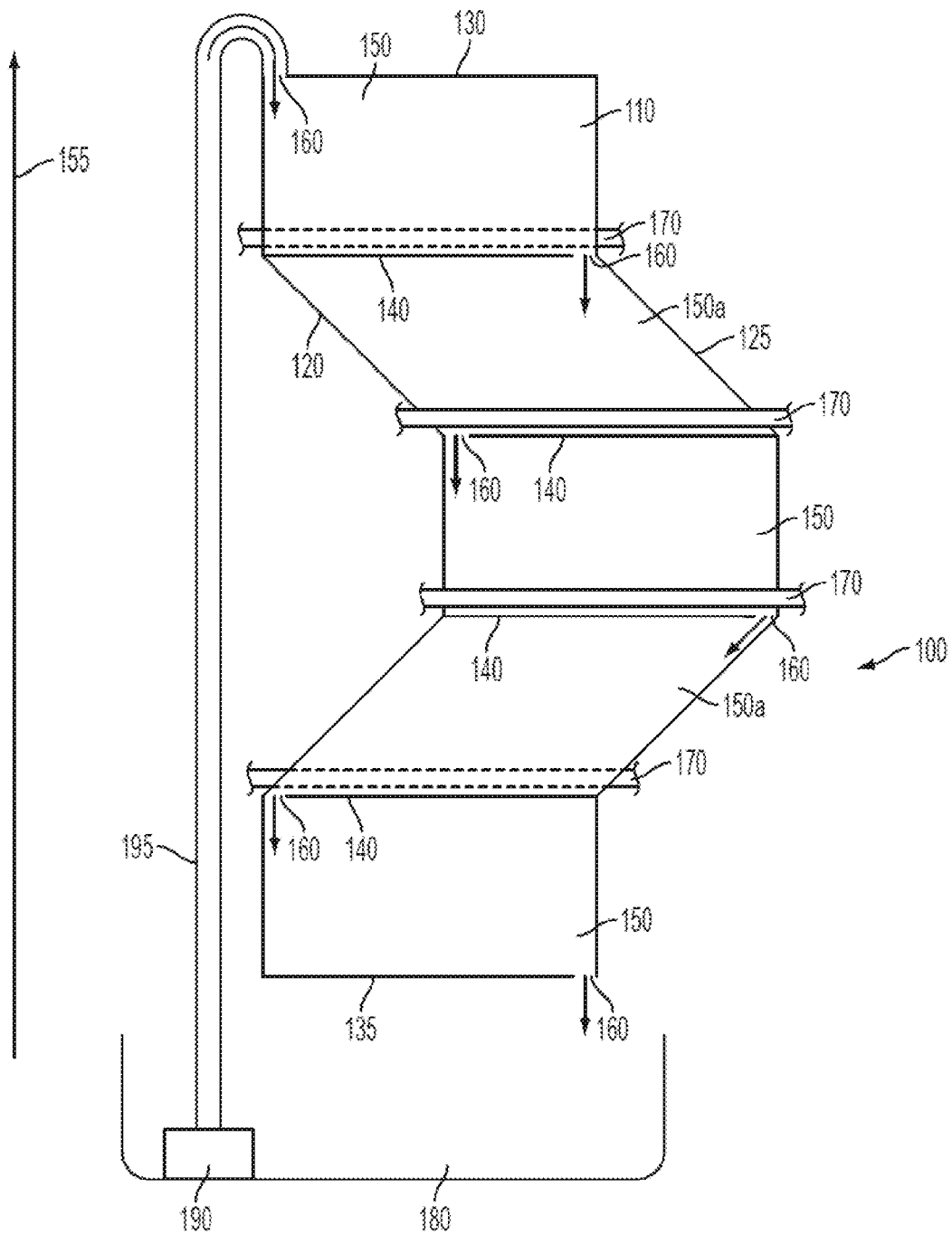
FIG. 1 is an elevation view of an exemplary bioreactor of the disclosure.

The ACClimatized bioreactOR for biomass proDuctION (ACCORDION) system disclosed herein provides highly efficient biomass production in a closed system with advantages of reduced costs for construction and operation (for example, low cost materials and reduced energy and water requirements), simplicity, modularity, and flexibility.

Although a bioreactor and method are described herein primarily with respect to algae culture (for example, the culture of microalgae), the disclosed bioreactor and method in their several embodiments are also suitable for culture of other photosynthetic cells, including for example, cyanobacteria. In other examples, the bioreactor and method are also suitable for culture of other cells and/or organisms, such as fungi, bacteria, viruses (such as algae, plant, bacterial, or fungal viruses), plant cells or plant tissue, and mammalian cells or tissue.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

I. Overview of Several Embodiments

Disclosed herein are bioreactors that include chambers arranged in series along a vertical axis, wherein each chamber is oriented at an angle relative to the vertical axis, wherein the angle is from about 0° to 90°. In some embodiments, the chambers are each oriented at alternating angles, such that the configuration suggests an accordion (e.g., FIGS. 2 and 4).

In some embodiments, a bioreactor includes:

(a) a first sheet and a second sheet, wherein the second sheet is disposed adjacent to the first sheet and the first and second sheets are sealed along a first longitudinal edge, a second longitudinal edge, a first horizontal edge, and a second horizontal edge, and comprising at least one intermediate horizontal seal between the first horizontal edge and the second horizontal edge, thereby forming at least two chambers for holding fluid in series along a vertical axis, wherein each of the two or more chambers is oriented at an angle relative to the vertical axis, wherein the angle is about 0° to about 90° and at least one of the chambers is oriented at an angle greater than 0°, and wherein there is at least one opening in each of the first horizontal edge, the second horizontal edge, and the at least one intermediate horizontal seal;

(b) a support structure comprising at least one horizontal support, wherein the horizontal support is located at or near the position of the intermediate horizontal seal;

(c) a reservoir below the second horizontal edge of the first and second sheets; and (d) means for pumping fluid from the reservoir to the first horizontal edge of the first and second sheets.

In some examples the first sheet and the second sheet are a flexible material, such as a flexible plastic, for example plastic sheeting. In particular examples, the sheets are flexible polyethylene, polyvinyl chloride, polypropylene, polyurethane, high density polyethylene, or polyacrylate. In a specific example, the sheets are polyethylene. In some examples the sheets are about 1 mil to about 10 mil thick (such as about 2 to 6 mil or 3 to 5 mil). In a particular example, the sheets are 3.5 mil thickness clear polyethylene sheeting (10 feet by 25 feet, Husky, part number RSHK3510-25C-U). In other examples, the first and second sheets are a rigid material. In particular examples, the rigid material is glass, Plexiglas, polycarbonate, or polyvinyl chloride. In some examples the rigid material is plastic (such as polyvinyl chloride or polycarbonate) having a thickness of about 0.5 mm to about 10 mm (such as about 1 to 10 mm or 2.5 to 7.5 mm). In other examples, the rigid material is glass having a thickness of about 1 mm to about 7.5 cm (for example about 10 mm to 5 cm or about 1 cm to 5 cm). In further examples, the first sheet and the second sheet are different materials. For example, the first sheet is a flexible material (for example, flexible polyethylene or polyvinyl chloride) and the second sheet is a rigid material (for example, rigid polyvinyl chloride or polycarbonate), or vice versa.

The size of the first and second sheets is selected to produce a bioreactor of a desired size. In some examples, the width of the first and second sheets (for example, from the first longitudinal edge to the second longitudinal edge) is about 2.5 cm to about 300 cm (for example, about 5-250 cm, 10-200 cm, 25-100 cm, 20-75 cm, or 30-60 cm). In a particular example, the width of the first and second sheets is about 45-55 cm. The material, thickness, and size of the sheets is selected such that the bioreactor does not substantially deform (for example, sag) or burst when the bioreactor is in operation. One of skill in the art can select suitable materials based on the expected weight of the bioreactor in operation, the arrangement of the support structure (discussed below), and the size of the chambers.

In further examples, at least one of the first and second sheets is transparent. In a particular example, both the first sheet and the second sheet are transparent. A transparent sheet is one that allows light of selected wavelengths to pass through (such as light of about 200 to 1000 nm or about 400 to 700 nm). In some examples, the transparent first and/or second sheets allow light of about 200 nm to 1000 nm to pass through. In some non-limiting examples, at least one of the first and second sheets allow photosynthetically active radiation (for example, wavelengths of light between about 400-700 nm) to pass through the sheet. In other examples, at least one of the first and second sheets is translucent or opaque (such as reflective). One of skill in the art can select appropriate materials and levels of transparency for the first and/or second sheets depending on the cells to be cultured in the bioreactor.

In some embodiments, the first sheet and the second sheet are disposed adjacent to one another. In some examples, the longitudinal (long) edges of the first and second sheet are closed or sealed, for example, along a first longitudinal edge and along a second longitudinal edge. The closure or seal is such that fluid that is between the first and second sheet cannot escape through the longitudinal edges. In one example, the longitudinal edges of the first and second sheets are sealed using a heat seal. In another example, the longitudinal edges of the first and second sheets are sealed using an adhesive. In some embodiments, the first and second sheets are also sealed along a first horizontal edge (for example, the "top" edge) and along a second horizontal edge (for example, the "bottom" edge). As discussed below, the first horizontal edge and the second horizontal edge are not sealed completely, and include at least one opening. When sealed along the first longitudinal edge, the second longitudinal edge, the first horizontal edge, and the second horizontal edge, the first and second sheet form a flattened tube. The length of the longitudinal edge of the first and second sheets determines the vertical height of a bioreactor of the disclosure. In some examples, the first and second sheets are at least 1 meter in length (such as about 1, 1.5, 2, 2.5, 3, 3.5, or more meters in length). In some examples, the first and second sheets are about 1.5-3 meters in length, such as about 2.5 meters in length.

In other embodiments, the first and second sheets are formed from a continuous sheet of flexible material. In some examples, a continuous sheet of the material is folded along a midpoint, such that the fold forms the first (or second) horizontal edge of a bioreactor. The material on one side of the fold forms the first sheet and the material on the other side of the fold forms the second sheet, which is disposed adjacent to the first sheet. The longitudinal edges are sealed and the open horizontal edge is sealed, forming the second (or first) horizontal edge. At least one opening is formed in each of the first and second horizontal edges, for example by cutting an opening, or incompletely sealing the edge. In other examples, a continuous sheet of the material is folded along a midpoint, such that the fold forms the first (or second) longitudinal edge of the bioreactor. The material on one side of the fold forms the first sheet and the material on the other side of the fold forms the second sheet, which is disposed adjacent to the first sheet. The second (or first) longitudinal edge is sealed and the open horizontal edges are sealed, forming the first and second horizontal edges. At least one opening is formed in each of the first and second horizontal edges, for example by cutting an opening, or incompletely sealing the edge.

In some examples, for example when air and/or fluid are present in the resulting flattened tube, the distance between the first sheet and the second sheet is about 5 mm to about 30 cm. In particular examples, the distance between the first sheet and the second sheet is about 1 cm to about 15 cm (such as about 1 to 10 cm, 1 to 5 cm, or 2 to 5 cm) when the bioreactor is in operation. In one specific example, the distance between the first and second sheet when the bioreactor is in operation is about 10 cm.

In some examples, the distance between the first and second sheet is not constant from the first longitudinal edge to the second longitudinal edge (for example, when a bioreactor is in operation). For example, the distance between the first and second sheet may increase from the first longitudinal edge to the approximate halfway point between the first and second longitudinal edges and may decrease from the approximate halfway point to the second longitudinal edge. Similarly, in some examples the distance between the first and second sheet is not constant from the top to the bottom of a chamber (for example, from the first horizontal edge to an intermediate horizontal seal, from an intermediate horizontal seal to the second horizontal edge, or between two intermediate horizontal seals) when a bioreactor is in operation. For example, the distance between the first and second sheet may increase from the first horizontal edge to an intermediate horizontal seal, from an intermediate horizontal seal to the second horizontal edge, or from one intermediate horizontal seal to the next intermediate horizontal seal.

The disclosed bioreactors include at least one intermediate horizontal seal located between the first horizontal edge and the second horizontal edge, forming at least two chambers for holding fluid in series along a vertical axis. In some examples, the intermediate horizontal seal is substantially horizontal, for example substantially parallel with the first and second horizontal edges. In other examples, the intermediate horizontal seal is angled, for example upwardly or downwardly from horizontal (for example, with respect to the first horizontal edge). In some examples, the angle is from about 30° to about 160° from horizontal. In other examples, the bioreactor includes a combination of orientations of the intermediate horizontal seals (such as horizontal, upwardly angled, downwardly angled, or any combination of two or more thereof). As discussed below, each intermediate horizontal seal includes at least one opening that allows communication of air and/or fluid between the two chambers. In some examples, the intermediate horizontal seal is formed (at least in part) by pressure from an exterior structure, such as the horizontal supports discussed below. In other examples, the intermediate horizontal seal is formed using a heat seal or an adhesive.

In some examples, the bioreactor includes two or more intermediate horizontal seals (such as 2, 3, 4, 5, 6, 7, 8, 9, 10, or more intermediate horizontal seals). In other examples, the bioreactor includes about 2-100 intermediate horizontal seals (such as about 5-100, 5-75, 5-50, 10-60, 20-80, or 10-50). Any number of intermediate seals can be used to produce a bioreactor with the desired number of chambers for holding fluid. The number and placement of the intermediate seals can also be chosen to form chambers of any desired size. For example, the intermediate horizontal seals can be placed in the first and second sheets so that the chambers are about 2.5 cm to about 60 cm (such as about 5-50, 10-40, 20-30, or 30-50 cm) in length (for example, from the first horizontal edge to the intermediate horizontal seal or from the intermediate horizontal seal to the second horizontal edge). In some examples, the intermediate seals are placed so that the chambers are approximately 30-40 cm in length. In other examples, the intermediate horizontal seals are placed so that the chambers are approximately 6 cm in length. In some examples, the one or more intermediate horizontal seals are placed such that the chambers formed are not of a uniform size. In one particular example, chambers that are oriented at an angle greater than 0° relative to the vertical axis are about 35 cm in length and chambers that are oriented at an angle of about 0° relative to the vertical axis are about 30 cm in length.

In some embodiments, the one or more intermediate horizontal seals are placed such that the ratio of the length to width (L/W ratio) of the chambers formed is about 1 (for example, about 0.8 to 1.2, such as about 0.9 to 1.1). In some examples, the L/W ratio is about 0.8, 0.9, 1.0, 1.1, or 1.2. In other examples, the L/W ratio is greater than about 1, for example, about 1.5, 2, 2.5, 3, 3.5, 4, 5, 6, 7, 8, 9, 10, or more. In further examples, the L/W ratio is less than about 1, for example, about 0.9, 0.8, 0.7, 0.6, 0.5, or less.

In some embodiments, the surface area and volume of the bioreactor are chosen to maintain a positive surface area to volume ratio. In particular examples, the bioreactor has a total surface area:volume ratio of about 12:1 to about 424:1. The surface area is the total surface area of the first and second sheets (the sum of the total length times total width for each sheet). The total volume is the total liquid volume that is held in the all of the compartments (excluding volume that remains in the reservoir).

The chambers are oriented at an angle with respect to a vertical axis, such as about 0° to about 90°. At least one of the chambers in a bioreactor is oriented at an angle greater than 0° relative to the vertical axis. In some examples, the angle is about 30° to about 75° or about 45° to about 65°. In other examples, the angle is about 5°, 10°, 15°, 20°, 25°, 30°, 35°, 40°, 45°, 50°, 55°, 60°, 65°, 70°, 75°, 80°, 85°, or 90°. The angle for each chamber in a bioreactor may be independently selected and is adjustable, such that the angles can be optimized for particular growing conditions (such as light conditions or cell type being cultured). In some examples, at least one of the chambers is oriented at an angle of about 0° relative to the vertical axis. In one particular example, a bioreactor has a configuration such that the chambers alternate between a chamber oriented at about 0° relative to the vertical axis and a chamber oriented at an angle greater than 0° relative to the vertical axis (e.g., FIGS. 2 and 3). In other examples, none of the chambers are oriented at an angle of about 0° relative to the vertical axis (for example, all of the chambers are oriented at an angle greater than 0° relative to the vertical axis, e.g., FIG. 4). As described herein, an "angle of about 0° relative to the vertical axis" does not require that the chamber be absolutely vertical. Thus, for example, an angle of about 0° relative to the vertical axis is one wherein the chamber is substantially vertical. In some examples, the angle may be up to about 2° relative to vertical (for example, about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2° relative to the vertical axis, e.g., FIG. 4). As described herein, an "angle of about 0) and still be considered to be about 0° relative to the vertical axis or substantially vertical.

The disclosed bioreactors include at least one opening in the first horizontal edge (the "top" edge), the at least one intermediate horizontal seal, and the second horizontal edge (the "bottom" edge). The openings allow flow of fluid through the bioreactor.

In some embodiments, the openings in each of the first and second horizontal edges are of a size sufficient to allow fluid (such as an algal culture) to enter the space between the first and second sheets (for example, through an opening in the first horizontal edge) and to exit the space between the first and second sheets (for example, through an opening in the second horizontal edge). In some examples, the openings are at least 1 cm wide (for example, 1 cm, 1.5 cm, 2 cm, 2.5 cm, or more). In a particular example, the opening in the first and/or second horizontal edge is about 2.5 cm wide. In another example, the opening in the first and/or second horizontal edge is about 5 cm wide. In other examples, the size of the openings is about 1-25% of the width of the chamber (such as about 5-25%, 1-15%, or 5-15%). In some examples, the first and/or second edges include two or more openings. In other examples, the size and/or number of openings in the first and second horizontal edges are not the same. For example, the first horizontal edge may have two openings and the second horizontal edge may have one opening.

The at least one intermediate horizontal seal also includes at least one opening, allowing flow of fluid from one chamber to the next along the vertical axis. In some examples, the opening is at least 1 cm wide (for example, 1 cm, 1.5 cm, 2 cm, 2.5 cm, or more). In a particular example, an opening in an intermediate horizontal seal is about 2.5 cm wide. In another example, an opening in an intermediate horizontal seal is about 5 cm wide. In other examples, the size of the openings is about 1-25% of the width of the chamber (such as about 5-25%, 1-15%, or 5-15%). In some examples, an intermediate horizontal seal includes two or more openings. In embodiments including two or more intermediate horizontal seals, the size and/or number of openings in each intermediate horizontal seal may not be the same. For example, one intermediate horizontal seal may have two openings and another intermediate horizontal seal may have one opening.

One of skill in the art can select an appropriate opening size (for example, in one or more of the first horizontal edge, second horizontal edge, and/or intermediate horizontal seal(s)), for example, taking into account the flow rate when the reactor is in operation. For example, larger opening may be selected if a higher flow rate is in use, in order to allow adequate flow throughout the entire system. Likewise, a smaller opening may be selected if a lower flow rate is in use.

In some embodiments, openings in the first horizontal edge, one or more intermediate horizontal seals, and/or the second horizontal edge are not aligned with one another in the vertical axis. For example, an opening in the top edge of a chamber is not directly aligned in the vertical axis with an opening in the bottom edge of the chamber (which is also the top edge of the next chamber in the vertical series). In one example, an opening in an intermediate horizontal seal is not aligned with an opening in the first horizontal edge. In another example, an opening in an intermediate seal is not aligned with an opening in the second horizontal edge. In other embodiments, at least two consecutive openings (for example, in the first horizontal edge, one or more intermediate horizontal seals, and the second horizontal edge) are aligned in the vertical axis. In some examples, all of the openings are aligned in the vertical axis, while in other examples at least two consecutive openings are aligned in the vertical axis.

Figure 5A:
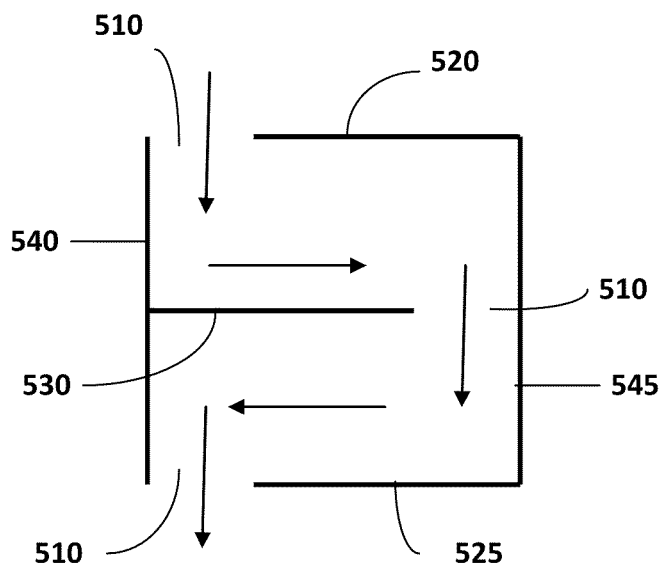
FIGS. 5A to 5D are diagrams showing exemplary layouts for openings in the first horizontal edge, second horizontal edge, and an intermediate horizontal seal in a bioreactor.
Figure 5B:
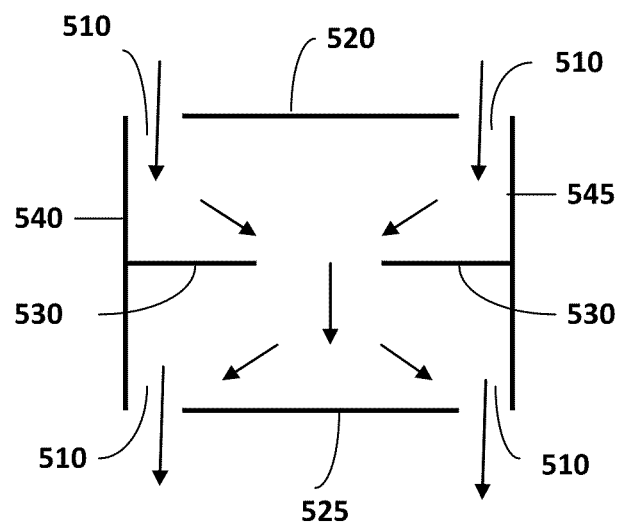
Figure 5C:
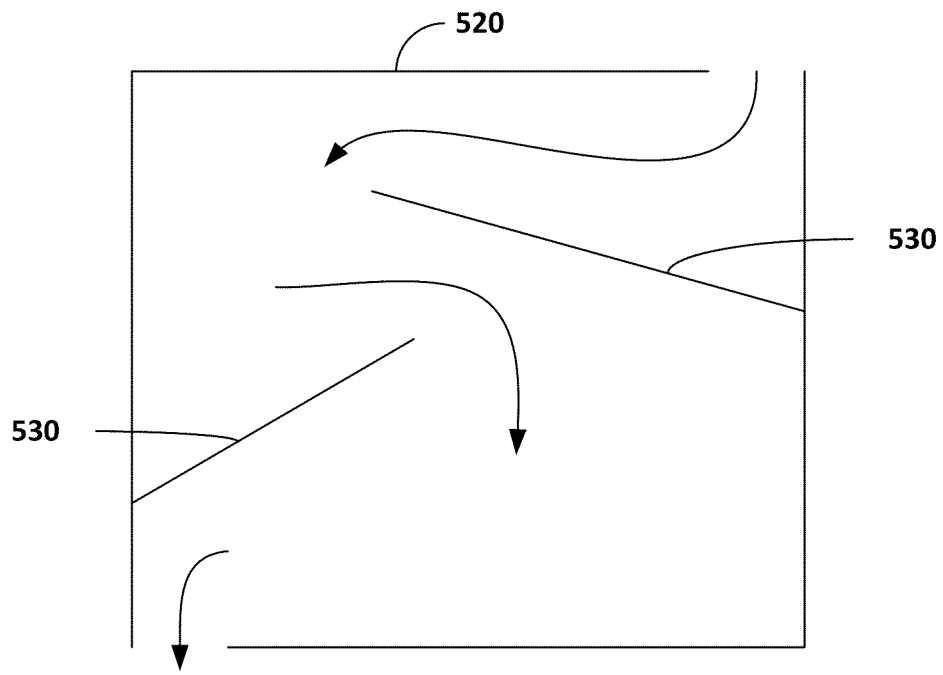
Figure 5D:
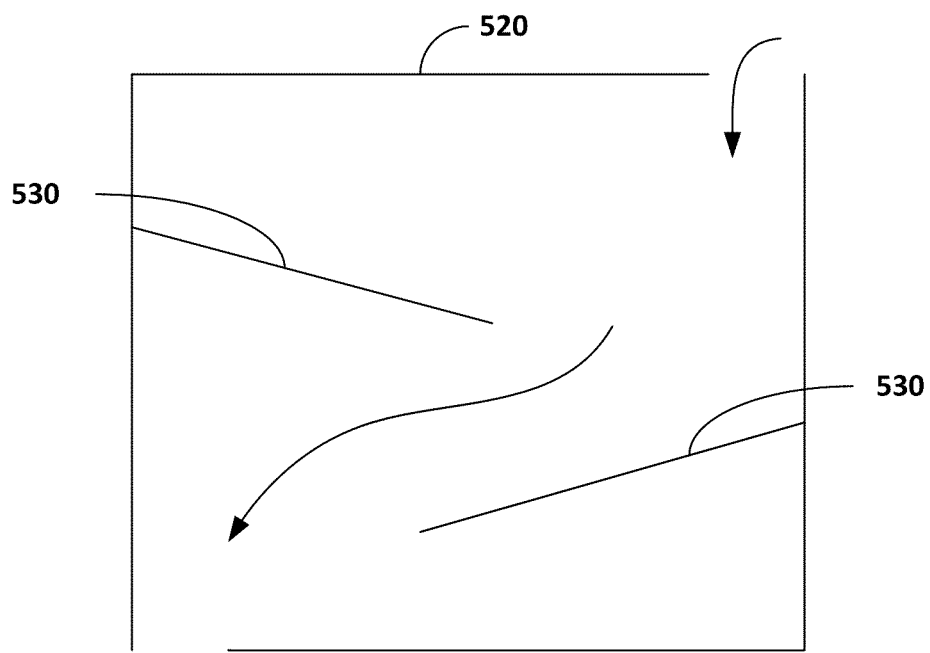

In one embodiment, the openings alternate between being adjacent to the first longitudinal edge and the second longitudinal edge, for example, producing a "serpentine" layout of openings (e.g., FIGS. 5A, 5C, and 5D). In a particular example, the opening in the first horizontal edge is adjacent (or near) to the first longitudinal edge, the opening in the intermediate horizontal seal is adjacent (or near) to the second longitudinal edge, and the opening in the second horizontal edge is adjacent (or near) to the first longitudinal edge. In another particular example, the opening in the first horizontal edge is adjacent (or near) to the second longitudinal edge, the opening in the intermediate horizontal seal is adjacent (or near) to the first longitudinal edge, and the opening in the second horizontal edge is adjacent (or near) to the second longitudinal edge. One of skill in the art can readily adapt this pattern to a bioreactor that includes more than one intermediate horizontal seal.

In another embodiment, the openings alternate between being adjacent (or near) to one or both of the longitudinal edges and at a position located between the longitudinal edges (e.g., FIG. 5B). In a particular example, the openings alternate between being adjacent (or near) to one or both of the longitudinal edges and at a position approximately halfway between the longitudinal edges. In a particular example, the first horizontal edge includes openings located adjacent (or near) to each of the longitudinal edges, the intermediate horizontal seal includes an opening at or near approximately halfway between the longitudinal edges, and the second horizontal edge includes openings adjacent (or near) to each of the longitudinal edges. In a particular example, the openings alternate between being adjacent (or near) to one or both of the longitudinal edges and at a position approximately halfway between the longitudinal edges. In another example, the first horizontal edge includes an opening at or near approximately halfway between the longitudinal edges, the intermediate horizontal seal includes openings located adjacent (or near) to each of the longitudinal edges, and the second horizontal edge includes an opening at or near approximately halfway between the longitudinal edges. One of skill in the art can readily adapt this pattern to a bioreactor that includes more than one intermediate horizontal seal.

The size, number, and layout of the openings are selected in order to produce hydrodynamic conditions suitable for growing the desired organism, cell, or tissue in the bioreactor. The hydrodynamic conditions may be characterized by parameters well known to one of skill in the art, such as dispersion number, residence time, and Reynolds number. See, e.g., Cuello and Ono, Fermentation Residence Time Distributions, In *Encyclopedia of Agricultural, Food and Biological Engineering*, Marcel Dekker Inc., New York, 2003. In some examples, the residence time is about 10 to 600 seconds (such as about 20-500 seconds, about 30-250 seconds, or about 40-150 seconds). In particular examples, the residence time is about 40-50 seconds or about 125-140 seconds. In other examples, the vessel dispersion number is about 0.005 to about 1000 (such as about 0.010-500, about 0.050-100, or about 0.100 to 50). In particular examples, the vessel dispersion number is about 0.100 to 0.250. In further examples, the Bodenstein number is about 0.001 to 200 (for example, about 0.010 to 100, about 0.050 to 20, or about 0.100 to 10). In specific examples, the Bodenstein number is about 4 to 8. In additional examples, the Reynolds number is about 300-4000 (such as about 300-3000, about 400-2000, or about 400-1000). In particular examples, the Reynolds number is about 450 to 900.

A bioreactor disclosed herein also includes a support structure that holds the first and second sheets and provides supports that allow the chambers to be angled relative to the vertical axis. In some embodiments, the support structure includes at least one horizontal support located at or near the level of the horizontal intermediate seal. In one example, a horizontal support is placed just above the level of each horizontal intermediate seal. In another example, a horizontal support is placed at about the same level as each intermediate horizontal seal. In further examples, a horizontal support is placed just below the level of each intermediate horizontal seal. In some examples, when the bioreactor includes more than one horizontal support, each horizontal support may be placed in a different location relative to each intermediate horizontal seal. For example, one horizontal support may be placed at about the same level as an intermediate horizontal seal and another horizontal support may be placed just above the level of another intermediate horizontal seal. In some examples, the at least one horizontal support is about 10 cm to about 10 m long (such as about 20 cm to 5 m, 50 cm to 2.5 m, or about 1 m). In other examples, the horizontal support may be more than 10 m long (for example 10, 25, 30, 25, 30, 40, 50, 60, 70, 80 90, 100 m, or more) provided that the material has sufficient strength to support the chambers without substantial bending or sagging. One of skill in the art can select an appropriate material (for example metal or plastic) according to the desired length and weight to be supported.

In a particular example, the bioreactor includes vertical supports (for example four vertical supports, for example in a square or rectangular arrangement) with horizontal supports connected between two vertical supports (for example, one or more horizontal supports extend between two of the vertical supports and one or more horizontal supports extend between the other two vertical supports). In some examples, the support structure may include one or more intermediate vertical supports, depending on the length of the horizontal supports. One of skill in the art can select the number and arrangement of vertical and horizontal supports based on the size and arrangement of the bioreactor.

In one particular example, the horizontal supports extend between two vertical supports that form the long side of a rectangle. In some examples, at least one horizontal support extends between the "front" long side of the rectangle, and at least one horizontal support extends between the "back" long side of the rectangle. The support structure is organized such that the horizontal supports can be offset from one another in a horizontal axis. For example, the horizontal supports may alternate between the front and back vertical supports, for example from top to bottom.

The chambers formed by the first and second sheet are disposed over or under the horizontal supports such that each chamber is approximately vertical (0° relative to the vertical axis) or at an angle relative to the vertical axis (for example from greater than about 0° to 90°). The horizontal and vertical supports are adjustable, so that the formation of the angles of the chambers can be altered simply and easily. One of skill in the art can select a suitable support structure. In some examples, commercial rack units are utilized. In other examples, a support structure can be constructed from readily available materials, such as polyvinyl chloride pipe or rods, metal bars or rods, or wooden bars or rods. In some examples, the support structure is about 1-4 meters in height. In other examples, the support structure is at least 1, 1.5, 2, 2.5, 3, 3.5, 4, 4.5, 5, or more meters in height. In a particular, non-limiting example, the support structure is a welded steel frame rack (such as Edsal model number ER2496) with steel horizontal beams (such as Edsal model number ER96).

A bioreactor disclosed herein also includes a reservoir or collection area (such as a basin or vessel) below the second horizontal edge of the first and second sheets. The reservoir is located such that fluid in the bioreactor flows from the at least one opening in the second horizontal edge into the reservoir. In some embodiments, the reservoir is located so that fluid flows from a single set of chambers formed from a first and second sheet into the reservoir. In other embodiments, the collection area is located so that fluid flows from two or more sets of chambers formed from two or more sets of first and second sheets into the reservoir (for example a modular bioreactor system, discussed below). In some examples, the volume of the reservoir is at least equal to 50% (such as at least 55%, 60%, 70%, 75%, 80%, 85%, 90%, 95%, 99% or even 100%) of the combined volume of the chambers formed in from the first and second sheets. In some examples, the volume of the reservoir is at least equal to the total volume of the chambers and any piping of the system. The shape of the reservoir can be selected by one of skill in the art, and can include any shape (for example, the collection area can be square, rectangular, circular, hexagonal, or any convenient shape).

The disclosed bioreactors also include means for pumping fluid (for example, a nutrient solution and/or a suspension of cells) from the reservoir to an opening in the first horizontal edge, such as a pump or other water displacement member. In some examples, the pump or displacement member includes an airlift pump, an axial flow pump, a centrifugal pump, a screw pump, a propeller pump, or a positive displacement pump. In some examples, the pump or displacement member is a submersible pump. In some embodiments, the pump returns fluid and/or culture to the first horizontal edge of a first and second sheet. In other embodiments, the pump returns fluid and/or culture to the first horizontal edge of two or more sets of first and second horizontal sheets (for example, in a modular bioreactor). In some examples, the pump means returns the fluid to the first horizontal edge via a pipe or tubing. In some examples, the fluid is returned through flexible tubing (such as polyethylene, rubber, Tygon®, or Teflon® polytetrafluoroethylene tubing). In other examples, the fluid is returned through a pipe (such as polyvinyl chloride or other rigid pipe material). Suitable materials can be selected by one of skill in the art. The tubing (or pipe) can be of any diameter sufficient to support the flow rate of the system, and can be selected by one of skill in the art. In some examples, the tubing or pipe has a diameter of about 0.5 cm to 20 cm (for example, about 0.5 cm to 10 cm, about 1 cm to 15 cm, or about 1 cm to 5 cm). In a particular example, the fluid is returned through Tygon® tubing of about 0.5 to 1 cm diameter.

In some embodiments, a bioreactor also includes at least one delivery device for providing carbon dioxide, air, other gases, and/or nutrients to the culture. In some examples, the at least one delivery device is placed in the reservoir. In other examples, a delivery device for providing gases and/or nutrients to the culture is placed in one or more of the chambers formed by the at least one intermediate horizontal seal. In some examples, gas is sparged into one or more of the chambers. In one example, gas sparging is included in all of the chambers. In some examples, the delivery device includes one or more carbon dioxide diffusers. In other examples, the delivery device includes one or more pipes for delivery of nutrients, for example a solution including salts (such as one or more of $KNO_3$, $K_2HPO_4$, $CaCl_2$, $MgSO_4$, $CoCl_2$, $H_3BO_3$, $MnCl_2$, $ZnSO_4$, $CuSO_4$, $Na_2MoO_4$, $H_2SO_4$, or citric acid) or other beneficial nutrients. In one example, a carbon dioxide and/or air delivery device is included in the reservoir. One of skill in the art can select appropriate gases and/or nutrients and their concentrations based on the organism, cell, or tissue present in an ACCORDION bioreactor.

Additional embodiments of the bioreactors disclosed herein do not include a reservoir. In such embodiments, the culture is directly recirculated from an opening in the second horizontal edge to an opening in the first horizontal edge via a conduit (such as a pipe or tubing as discussed above) utilizing a pump or other water displacement member. In the absence of a reservoir, the at least one delivery device for providing gases and/or nutrients is placed in one or more of the chambers. The culture can be continuously recirculated or can be held in the chambers in this embodiment.

In some embodiments one or more sensors are optionally included. In some examples, sensors and instrumentation are included to monitor one or more parameters of the algae culture, the environment, or both. Culture parameters that may be monitored include water temperature, electrical conductivity, pH, carbon dioxide, dissolved oxygen, optical density (e.g., algal density), ion concentration (e.g., calcium concentration) and flow rate. Environmental parameters that may be monitored include air temperature, relative humidity, solar radiation, photosynthetic active radiation, and wind speed. The sensors for measuring culture parameters are placed in one or more locations in the system, for example, at least one sensor is placed in the reservoir. One of skill in the art can select appropriate numbers and locations for sensors for any particular parameter. One or more sensors for monitoring environmental parameters are placed in close proximity to the bioreactor, such as within at least 50 meters of the bioreactor.

In additional embodiments, the disclosed bioreactors include means for regulating temperature of a culture in the bioreactor. In some examples, a bioreactor includes a heating or cooling jacket (for example integrated in one of the first and second sheets) that can be used to regulate the temperature of a culture. Means of regulating temperature of a bioreactor are well known to one of skill in the art and include heat exchangers, such as by circulating a heated or chilled liquid through a jacket in order to maintain a constant selected temperature. In some examples, a third sheet of transparent material (such as flexible plastic sheeting) is placed over one or both of the first and second sheets, creating a second layer that fluid (such as water of a desired temperature) is re-circulated through. The thickness of the layer and the fluid are selected such that there is not a substantial decrease in light passing through the second layer to the space between the first and second sheet. In other examples, temperature regulation is achieved by spraying the outer surface of the reactor chambers with a fluid (such as water), creating evaporative cooling. In further examples, a temperature regulation means, such as a coil or tube heat exchanger is inserted into the reservoir in order to regulate temperature. Heat sinks or heat transfer fins can be inserted into the wall of the reservoir in order to passively increase the heat exchange with the surrounding air. In some examples, heat for the heating jacket or heat exchanger is waste heat, for example from a biogasification system, solar cell waste heat unit, power plant, geo-thermal source, or industrial plant located near the system. In other examples, heat for the heating pipe is provided from warm water. In further examples, the temperature regulation device includes at least one cooling pipe, such as a pipe for circulating cool water.

The disclosed bioreactors can be arranged in a modular fashion. For example, a common structural support (such as the at least one horizontal support) can be used to support multiple vertical series of chambers as described above. FIG. 6 shows an exemplary modular system with three vertical series of chambers. The number of vertical series of chambers can be selected by one of skill in the art based on the desired level of production of culture, size of the chambers, and size of the support structure. In some non-limiting examples, the number of vertical series of chambers is 1 or more (such as 2, 3, 4, 5, 6, 7, 8, 9, 10, or more). In other non-limiting examples, the number of vertical series of chambers is 2-50 (such as 5-30 or 10-20). In particular examples, the modular system includes at least four vertical supports (for example, in a rectangular configuration) and at least one horizontal support that extends between two of the vertical supports. Multiple vertical series of chambers can be supported by the same horizontal support(s).

In some examples, the system including two or more vertical series of chambers share a common reservoir, one or more pumps, and/or one or more delivery devices for providing carbon dioxide, air, other gases, and/or nutrients to the culture. In other examples, each of the vertical series of chambers has a separate reservoir, pump, and optionally a delivery device for providing carbon dioxide, air, other gases, and/or nutrients to the culture.

II. Description of Particular Embodiments

In the drawings provided herein and described below, it is to be understood that the drawings are exemplary only and are not necessarily shown to scale. Any of the features described herein (for example, length and/or width of the sheets, size of openings, size of chambers, angles, size of structural supports, and so on) can be adjusted by one of skill in the art utilizing the present disclosure.

FIG. 1 is an elevation view of an exemplary embodiment of a bioreactor 100 of the disclosure. The bioreactor includes a first sheet 110 disposed adjacent to a second sheet (not shown), which are sealed along a first longitudinal edge 120 and a second longitudinal edge 125. The first sheet 110 and second sheet (not shown) are also sealed along a first horizontal edge 130 and a second horizontal edge 135 and are also have at least one intermediate horizontal seal 140 between the first horizontal edge 130 and the second horizontal edge 135. The intermediate horizontal seal 140 forms at least two chambers 150 capable of holding fluid. The chambers are in series along a vertical axis 155, wherein each of the at least two chambers 150 are oriented at an angle from 0° to 90° relative to the vertical axis and at least one of the chambers 150a is oriented at an angle greater that 0° relative to the vertical axis. There is at least one opening 160 in each of the first horizontal edge 130, the second horizontal edge 135, and the at least one intermediate horizontal seal 140, for example to allow fluid flow through the chambers. The bioreactor 100 also includes a support structure that includes at least one horizontal support 170 that is positioned at or near the at least one intermediate horizontal seal 140. The bioreactor 100 also includes a reservoir 180 below the second horizontal edge 135 and a means for pumping fluid from the reservoir 180 to the opening 160 in the first horizontal edge 130, for example a pump 190 and a conduit 195. The arrows show the direction of fluid flow.

Figure 2:
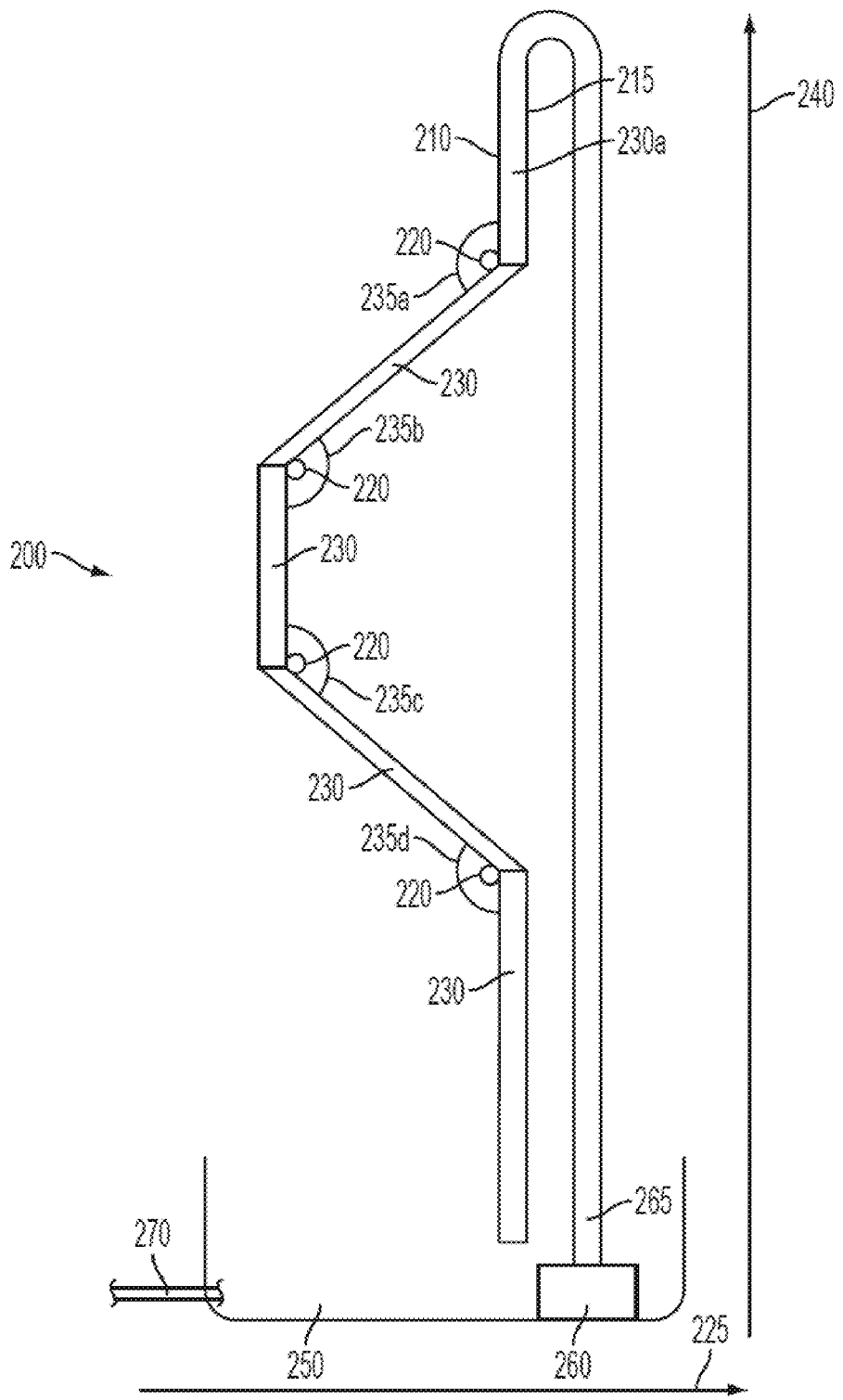
FIG. 2 is a side view of an exemplary bioreactor of the disclosure having chambers alternating between about 0° relative to vertical and an angle greater than 0° relative to vertical.

FIG. 2 is a side view of an exemplary embodiment of a bioreactor 200 of the disclosure. A first sheet 210 is disposed adjacent to a second sheet 215. As shown in this view, at least some of the horizontal supports 220 are offset in a horizontal axis 225 to support the chambers 230 at an angle 235 relative to the vertical axis 240. Each of the angles (235a, 235b, 235c, and 235d) can be different, or two or more can be the same (for example, 235b and 235c may be the same. The reservoir 250 includes a pump means 260 and a conduit 265 (for example, tubing) to return fluid to the top chamber 230a. In this embodiment, the reservoir 250 also includes at least one inlet line 270 for introducing gases and/or nutrients into the reservoir 250.

Figure 3:
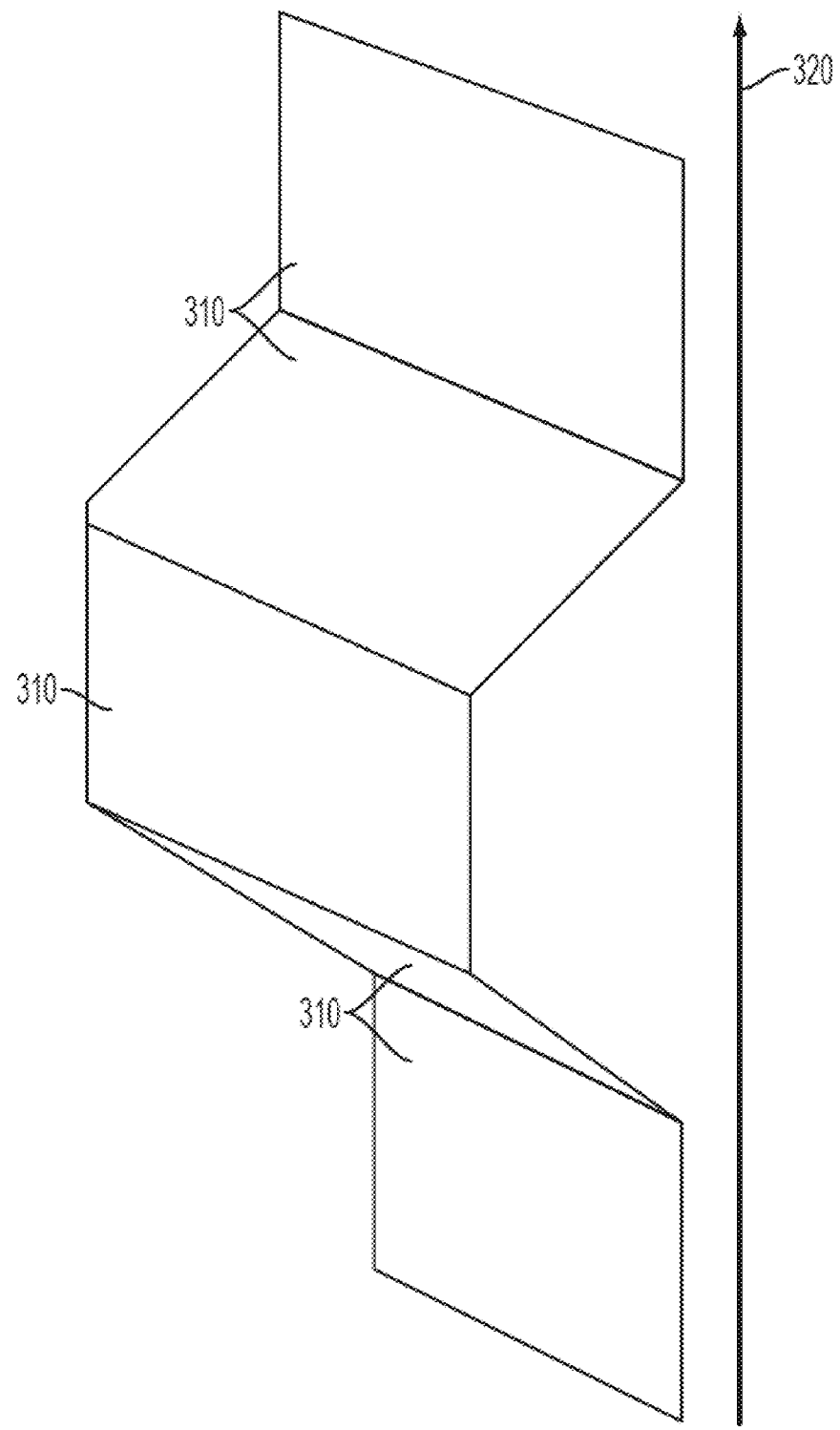
FIG. 3 is a perspective view showing a portion of an exemplary bioreactor of the disclosure.

FIG. 3 is a perspective view of a portion of an exemplary bioreactor 300 of the disclosure showing the arrangement of the chambers 310 with respect to the vertical axis 320.

Figure 4:
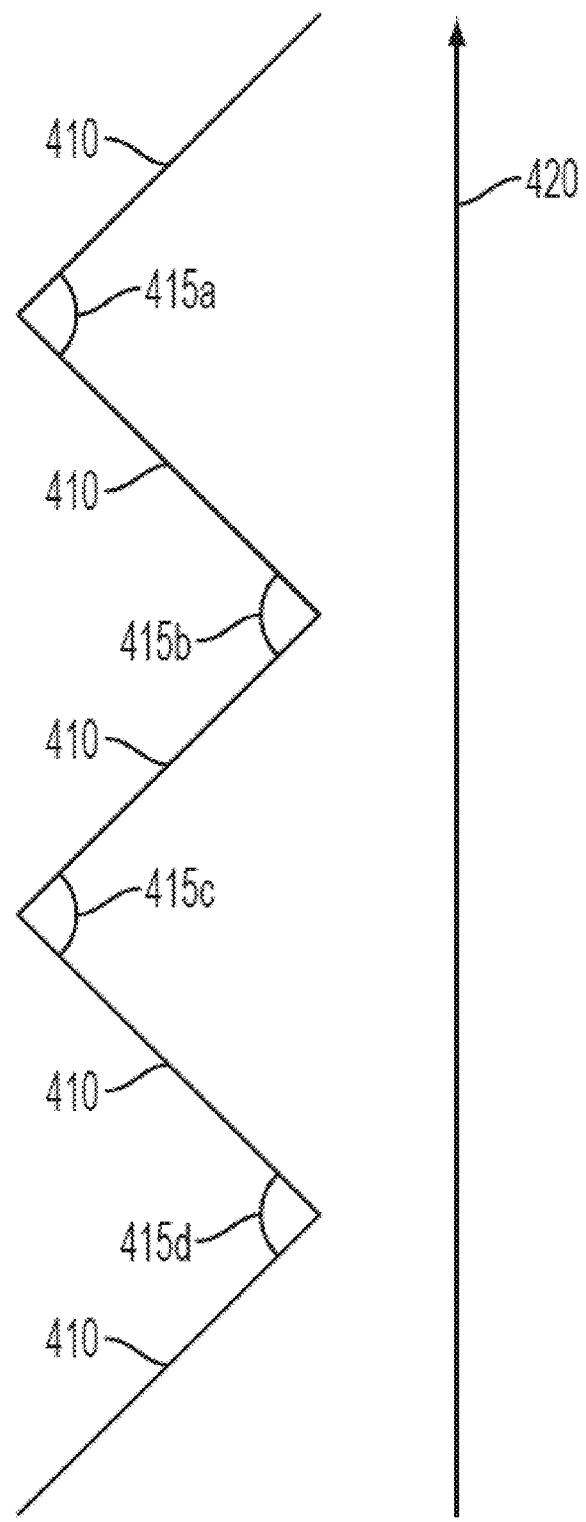
FIG. 4 is a side view of an exemplary bioreactor of the disclosure having all chambers oriented at an angle greater than 0° relative to vertical.

FIG. 4 is a side view of the arrangement of chambers of an exemplary embodiment of a bioreactor of the disclosure. Each of the chambers 410 is oriented at an angle 415 greater than 0° relative to the vertical axis 420. Each of the angles (415a, 415b, 415c, and 415d) can be different, or two or more (or all) can be the same.

FIGS. 5A through 5D are flattened elevation views of exemplary patterns of openings in the chambers of the disclosed bioreactors. In FIG. 5A, the openings 510 in the first horizontal edge 520, second horizontal edge 525, and intermediate horizontal seal 530 alternate between being adjacent to the first longitudinal edge 540 and the second longitudinal edge 545. In FIG. 5B, the first horizontal edge 520 has two openings 510, one adjacent to the first longitudinal edge 540 and one adjacent to the second longitudinal edge 545. The intermediate horizontal seal 530 has one opening 510 that is approximately in the center of the intermediate horizontal seal 530. The second horizontal edge 525 has two openings 510, one adjacent to the first longitudinal edge 540 and one adjacent to the second longitudinal edge 545. In FIG. 5C, the intermediate horizontal seals 530 are angled upwardly relative to the first horizontal edge 520. In FIG. 5D, the intermediate horizontal seals 530 are angled downwardly relative to the first horizontal edge 520. Arrows indicate the general direction of fluid flow in the bioreactor.

FIG. 6 is an elevation view showing an exemplary modular arrangement of a disclosed bioreactor. The horizontal supports 610 can hold multiple ACCORDION bioreactors 620. In an exemplary embodiment, each bioreactor 620 includes an individual reservoir 630. However, in other embodiments, the system can include a single reservoir for multiple bioreactors.

III. Methods of Culturing Cells in an Accordion Bioreactor

Disclosed herein are methods of culturing cells in a bioreactor utilizing embodiments of the ACCORDION bioreactor described above.

In one embodiment, the method includes circulating a suspension of cells in a nutrient solution in a bioreactor of the present disclosure. In another embodiment, the method includes circulating a fluid (such as a nutrient solution) in a bioreactor of the disclosure, wherein one or more of the chambers of the bioreactor contain cells or tissue in culture. The methods include both batch culture and continuous culture of the cell and/or organism of interest.

In some embodiments, the culture and/or fluid is circulated from a reservoir located below the second horizontal edge of the first and second sheets to the first horizontal edge of the first and second sheets. The culture and/or fluid flows down through the series chambers formed by the intermediate horizontal seals by gravity flow. The culture and/or fluid returns to the reservoir through the opening in the second horizontal edge of the first and second sheets. The culture and/or fluid is transported from the reservoir to the first horizontal edge by means of one or more pumps or displacement members. In some examples, the pump is a submersible pump that is placed in the reservoir. In other embodiments the culture and/or fluid is circulated from an opening in the second horizontal edge to an opening in the first horizontal edge for example, in embodiments of the ACCORDION bioreactor that do not include a reservoir.

In some examples, the pump provides a flow rate of about 5 to 70 liters per minute (such as about 5 to 50, 10 to 70, 15-50 liters/minute). In one particular example, the pump provides a flow rate of about 14 liters/minute at a head of 8 feet. Additional pumps can be added to increase the flow rate, for example to about 28 liters/minute or about 42 liters/minute. Alternatively a regulator valve or a variable drive pump can be used to regulate the flow rate. The culture and/or fluid is transported from the reservoir (or from the second horizontal edge) to the first horizontal edge by a conduit or pipe. In a particular example, the conduit is tubing, such as flexible tubing (for example, polyethylene, rubber, Tygon®, or Teflon® tubing).

In some embodiments, the method includes varying the flow rate in order to adjust the hydrodynamic conditions. For example, homogeneous flow is created by low flow velocity. In some examples, homogeneous flow is created by low flow velocity in combination with conditions of uniform flow (for example, two or more consecutive openings are aligned in the vertical axis) and/or limited mixing. In other examples, heterogeneous flow is created by high flow velocity. In some examples, heterogeneous flow is created by high flow velocity in combination with conditions of chaotic flow (for example, serpentine or alternating pattern of openings) and/or high mixing. One of skill in the art can select a flow rate to create the desired flow and hydrodynamic conditions for a disclosed bioreactor.

In some embodiments, the method includes exposing the bioreactor, and the culture in the bioreactor to a light source, for example for culture of photosynthetic cells, such as algae. In some examples, the light source is natural sunlight. For example, the bioreactor may be placed outdoors or in a greenhouse where it is exposed to natural sunlight. In this example, the culture is exposed to natural light/dark cycles, which vary in length according to latitude and season. In other examples, the bioreactor and culture is exposed to an artificial light source (for example, incandescent, fluorescent, or halogen lamps, or light emitting diodes). If the light source is an artificial light source, the method may include alternating periods of light and dark. In one example, the bioreactor is exposed to light for 12 hours of a 24 hour cycle.

In some examples, the wavelength of the light source (such as an artificial light source) is selected to promote optimal growth of the organism or cell type in culture in the bioreactor. In some examples, the wavelength of the light source includes or consists of photosynthetically active radiation (for example, wavelengths of light between about 400-700 nm). In other examples, the wavelength of the light source is selected to induce or increase synthesis of one or more compounds of particular interest by the organism or cell in culture. For example, synthesis of anthocyanin is induced by UV-B light (such as about 280-300 nm). One of skill in the art can select appropriate lights or wavelengths for culture of cells and/or production of compounds of interest, for example to maximize cell growth or production.

In some examples, the angle of one or more of the chambers of the bioreactor relative to the vertical axis is selected to optimize the exposure of the chamber (and the culture within) to incident light. In some examples, the angle of one or more of the chambers is selected such that the irradiance of at least one chamber is about 80 to 500 mmol/m²s. One of skill of the art can select an appropriate irradiance range, based on the cell or organism that is in culture in the bioreactor. In some examples, an irradiance of about 80-250 µmol/m²s is selected if microalgae is in culture. In other examples, an irradiance of about 300-400 mmol/m²s is selected if plant cells or plant tissue is in culture. In some examples (for example, if the bioreactor is exposed to natural sunlight), the angle necessary to achieve a selected irradiance may change over time. The bioreactor can be adjusted (for example, by moving one or more horizontal supports) in order to change the angle of one or more of the chambers to achieve or maintain a selected irradiance level. In some examples, this is achieved by manually adjusting the bioreactor. In other examples, an automated system is used to periodically or continuously adjust the angle of one or more of the chambers to achieve or maintain the selected irradiance.

In some examples, the method includes regulating the temperature of the culture. Means for temperature regulation are well know to one of skill in the art. In one example, the bioreactor is in an enclosed area (such as a greenhouse) which is heated or cooled to maintain a selected temperature or range of temperatures. In other examples, the temperature of the culture may be regulated by a temperature regulation device in or around the reservoir and/or the bioreactor chambers. Such devices include heating or cooling jackets or heat exchangers (as discussed in section I, above). In particular examples, heat is provided at night in order to maintain the temperature of the culture in an optimal range for growing the culture. In other examples, cooling is provided during the day (particularly at times of day or seasons with high solar radiation) in order to maintain the temperature of the culture in an optimal range. One of skill in the art can select appropriate temperature ranges for the particular cell or organism in culture and determine the need for heating or cooling to maintain the selected temperature range.

In some embodiments, the method also includes harvesting the culture. The culture may be harvested when a selected parameter is reached, for example a time point (for example, at least about 24, 36, 48, 72, 96, or more hours of culture), cell density (for example, at least about $10^3$, $10^4$, $10^5$, $10^6$, or more cells per milliliter), or optical density of the culture (for example, absorbance of at least about 0.5, 1.0, 1.5, 2, 2.5, or more at a selected wavelength). One of skill in the art can select appropriate parameters or time points for culture harvest, based on the organism or cell type being cultured.

Methods for harvesting cells are well known to one of skill in the art. In some examples, the entire culture is harvested. In other examples, a portion of the culture is retained (for example, in the reservoir) for use as inoculum for continued culture production. For example, culture is stored for use as an inoculum and water is subsequently added to the bioreactor to start the new culture batch. In some examples, the culture stored for inoculum use is about 100 ml to about 100 liters (such as about 1-50 liters, 10-75 liters, 25-75 liters, or about 50 liters). In other examples, a proportion of the culture is retained for inoculation of the new culture, for example about 10-50% of the total harvested culture volume (such as about 10-40%, 10-35%, 20-50%, 20-40%, 30-35%, or about 33% of the total harvested culture volume). The volume or percentage of the culture needed for use as inoculum can be determined by one of skill in the art, for example, based on the cell or organism in culture, the density of the culture at harvesting, and the total volume of water that will be inoculated.

The bioreactors and methods disclosed herein are suitable for culturing a wide variety of organisms or cells, including, but not limited to algae (such as microalgae and/or macroalgae). In some examples, the algae species include, but are not limited to *Chlorella* (such as *Chlorella vulgaris*), *Chlamydomonas* (such as *Chlamydomonas reinhardtii*), *Chaetoceros, Spirulina* (such as *Spirulina platensis*), *Dunaliella*, and *Porphyridum*. In particular examples, the algae species include algae useful for production of biofuels or other compounds (such as polyunsaturated acids, pigments, or phytochemicals, for example, for nutritional supplements). In some examples, the algae include *Akistrodesmus, Arthrospira, Botryococcus braunii, Chlorella* (such as *Chlorella* sp. or *Chlorella protothecoides*), *Crypthecodinium* (such as *Crypthecodinium cohnii*), *Cyclotella, Dunaliella tertiolecta, Gracilaria, Hantzschia, Haematococcus* (such as *Haematococcus pluvialis*), *Nannochloris, Nannochloropsis, Neochloris oleoabundans, Nitzschia, Phaeodactylum, Pleurochrysis carterae* (also called CCMP647), *Porphyridium, Sargassum, Scenedesmus* (such as *Scenedesmus obliquus*), *Schiochytrium, Stichococcus, Tetraselmis suecica, Thalassiosira pseudonana, Thraustochytrium roseum*, and *Ulkenia* sp. In one example, the algae species is *Botryococcus braunii*.

The bioreactors and methods disclosed herein are also suitable for culturing any cells that can be grown in suspension, including but not limited to, microalgae (as discussed above), macroalgae, bacteria (e.g., *Escherichia coli, Bacillus subtilis*, or *Corynebacterium*), fungi (e.g., *Saccharomyces cerevisiae, Kluyveromyces lactis*, or *Pischia pastoris*), insect cells (e.g., *Spodoptera frugiperda* cells (such as Sf9 or Sf21 cells) or *Trichoplusia ni* cells (such as High Five™ cells)), plant cells (such as *Arabidopsis thaliana* cells, *Nicotiana tabacum* cells, or *Taxus* cells), or mammalian cells (such as Chinese hamster ovary (CHO) cells). In one example, the bioreactors and methods disclosed herein are useful for culturing algae for the production of fatty acids for synthesis of biofuels. In other examples, the bioreactors and methods disclosed herein are useful for culturing cells for the production of other natural products (such as taxols, pigments, or dietary supplements) or recombinant proteins.

The bioreactors and methods disclosed herein may also be used for culture of tissue or organs (such as animal or plant tissue or organ culture). In one example, the bioreactors and methods disclosed herein are used for hairy root culture (for example *Panax ginseng, Lithospermum erythorhizon, Hyoscyamus muticus*, or *Atropa belladonna*). In other examples, the bioreactors and methods disclosed herein may be used to culture plant tissue, plant organs, or plant somatic embryos. In other examples, the bioreactors and methods disclosed herein may be used to culture mammalian organs or mammalian tissue. In some examples, the tissue or organ is stationary in one or more chambers of a bioreactor and nutrient solution flows through the compartment, submerging or bathing the tissue or organ.

The present disclosure is illustrated by the following non-limiting Examples.

EXAMPLES

Example 1

Algal Cultures

This example describes the algae strains and laboratory culture conditions for algae utilized in photobioreactor experiments.

*Botryococcus braunii* strain UTEX 572 was obtained from the University of Texas Culture Collection (Austin, Tex.). *B. braunii* is a single-celled green algae species that has been noted in the literature for its high content of long chain hydrocarbons. The strain was grown under sterile conditions in a modified Chu 13 culture medium of pH 7.5 (Table 1) prepared using Millipore® filtered distilled water. After preparation, the media was autoclaved with a sterilization hold of 25 minutes at 121° C. Laboratory cultures were maintained in 500 ml flasks under an illumination of 150-200 µmol/m²s from cool white fluorescent bulbs. The cultures received 12 hours of illumination every day. Air that had been enriched with 5% $CO_2$ was continuously supplied to the culture. Culture flasks were kept continuously mixed by using a magnetic stirrer. Healthy cells were harvested every 7-10 days and re-suspended in fresh media.

TABLE 1

Chu 13 media recipe

| Compound | mg/L |
|---|---|
| $KNO_3$ | 371 |
| $MgSO_4$—$7H_2O$ | 200 |
| $CaCl_2$—$2H_2O$ | 107 |
| $C_6H_8O_7$ | 100 |
| $K_2HPO_4$ | 80 |
| $Fe(C_6H_5O_7)$—$5H_2O$ | 20 |
| $H_3BO_3$ | 2.86 |
| $MnCl$—$4H_2O$ | 1.81 |
| $Na_2MoO_4$—$2H_2O$ | 0.39 |
| $ZnSO_4$—$7H_2O$ | 0.22 |
| $CuSO_4$—$5H_2O$ | 0.08 |
| $Co(NO_3)_2$—$6H_2O$ | 0.05 |

All *B. braunii* photobioreactor experiments (e.g., Example 3) were also conducted with the same modified Chu 13 media. The photobioreactors were not maintained under sterile conditions but were routinely cleaned and disinfected. All photobioreactor experimental trials were inoculated with fresh algae cultures that had been grown in the laboratory under sterile conditions. All photobioreactor experiments were carried out using the same 5% $CO_2$ enriched supply of air.

Experiments were also conducted with *Nannochloropsis occulata*, which is a saltwater strain of green algae. *N. occulata* (LB 2164) was obtained from the UTEX culture collection and is noted in the literature for producing highly unsaturated fatty acids such as omega-3 fatty acids. The cultures were grown in modified F/2 medium utilizing an artificial seawater mix (Table 2). The culture was maintained under the same laboratory conditions that were listed above for *B. braunii*.

TABLE 2

F/2 medium and artificial seawater recipe

| Compound | Concentration (g/L) | |
|---|---|---|
| $NaNO_3$ | 0.15 | nutrient |
| $NaH_2PO_4$—$H_2O$ | 0.01 | nutrient |
| $FeCl_3$—$6H_2O$ | 0.0013 | Micro nutrient |
| $Na_2EDTA$-$2H_2O$ | 0.0087 | Micro nutrient |
| $CuSO_4$—$5H_2O$ | $9.8 \times 10^{-9}$ | Micro nutrient |
| $Na_2MoO_4$—$2H_2O$ | $6.3 \times 10^{-9}$ | Micro nutrient |
| $ZnSO_4$—$7H_2O$ | $2.2 \times 10^{-8}$ | Micro nutrient |
| $CoCl_2$—$6H_2O$ | $1.0 \times 10^{-8}$ | Micro nutrient |
| $MnCl_2$—$4H_2O$ | $18 \times 10^{-8}$ | Micro nutrient |
| B12 Vitamin | $5 \times 10^{-7}$ | vitamin |
| Biotin | $5 \times 10^{-7}$ | vitamin |
| NaCl | 23.375 | Artificial Seawater |
| $MgSO_4$—$7H_2O$ | 4.925 | Artificial Seawater |
| $CaCl_2$—$2H_2O$ | 1.11 | Artificial Seawater |
| KBr | 0.2025 | Artificial Seawater |
| KCl | 0.745 | Artificial Seawater |
| $MgCl_2$—$6H_2O$ | 4.0625 | Artificial Seawater |
| $H_3BO_3$ | 0.01263 | Artificial Seawater |

Example 2

Measurement of Algae Biomass

This example describes the methods utilized to determine algae biomass in a sample.

The amount of algae biomass contained in a sample was determined both by directly measuring the dry weight and the optical density of a sample. Dry weight measurements were performed by obtaining a sample and centrifuging at 3000 g for 8 minutes. The resulting clear fluid, containing nutrient media and other organic compounds, was discarded and the remaining pellet of algae biomass was re-suspended in a matching volume of deionized (DI) water. Whatman GF/A glass fiber filters that had been previously weighed were then used to separate the biomass from the liquid component. After filtering, the sample retained on the filter paper was washed with 10 ml of dilute HCl with a pH of 4.0. The samples were then rinsed with DI water and placed in an 80° C. oven for 24 hours. Finally, the filter papers were weighed and the increase in mass due to retention of algae biomass was recorded. The weight of the biomass was divided by the volume of the sample that was filtered in order to obtain a measure of biomass density in units of grams per liter.

Figure 7:
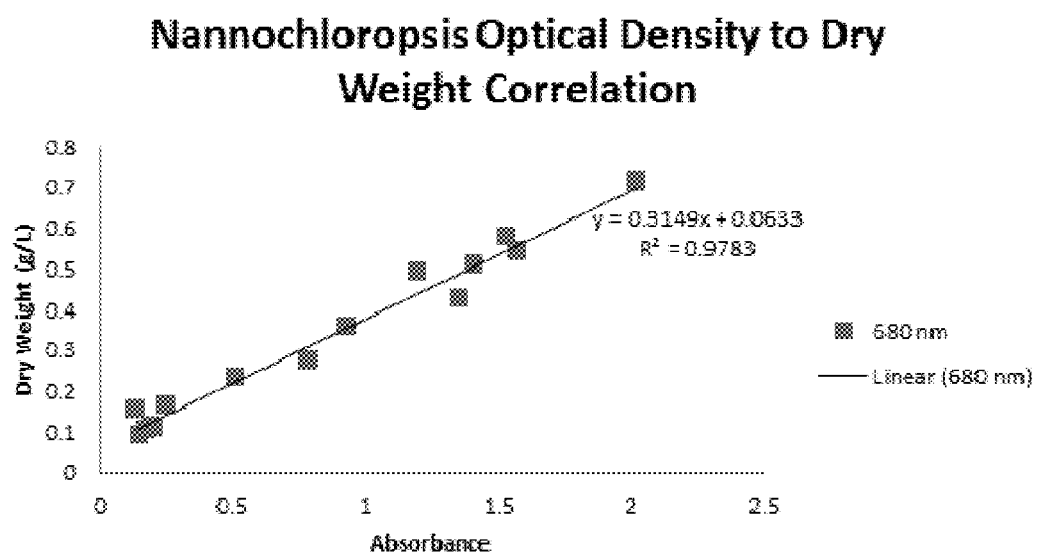
FIG. 7 is a graph showing correlation of *Nannochloropsis* culture optical density and dry weight (g/L).

The optical density of a sample was determined using a Beckman spectrophotometer, measured in a 1 ml cuvette. Absorption readings were taken at 540 nm, 680 nm, and 750 nm. The peak absorption occurred at 680 nm. Samples with a high density were diluted until the absorption readings were within an optimal range of 0.10 to 0.40 to minimize any mutual shading of cells, which can lead to erroneously low absorption readings. Optical density measurements were recorded for every sample from every experimental treatment. Dry weight measurements were also recorded for three random treatments every time samples were taken. In doing so, a standard curve correlating optical density measurements to dry weight of algae biomass was established. Results of the correlation were also verified by performing the same sampling routine with algae cultures maintained in the laboratory. A linear regression of the relationship between optical density at 680 nm and cell dry mass produced an $R^2$ value of 0.9783 (FIG. 7), resulting in a suitable calibration equation that can be used to convert optical density measurements to dry cell mass estimates.

Plotting dry cell mass versus time results in a growth curve that illustrates many of the properties associated with the culture health and growth. The specific biomass growth rate ($\mu_{dw}$) can be determined by fitting regression equations to the exponential portion of the growth curve and fitting the regression to the theoretical exponential cell growth equation:

$$C = C_0 e^{\mu_{DCM} t}$$

where C represents the cell concentration in grams dry cell mass per liter (g DCM L$^{-1}$), $C_0$ is the initial cell concentration in g DCM L$^{-1}$, and t is time in hours.

Example 3

ACCORDION Bioreactor Construction and Testing

This example describes the construction of an ACCORDION bioreactor and initial culture of microalgae.

A 50-70 L test unit was constructed. A simple frame was constructed from PVC plastic in order to support the flexible polyethylene reactor chambers. The PVC frame allowed for easy adjustment of the supporting beams and for changing the size and positioning of the reactor chambers. The frame was originally constructed with a height of 2.13 meters, a width of 0.61 meters, and a depth of 0.43 meters. The polyethylene sheeting including the chambers was attached to the frame by anchoring the top edge of the polyethylene to the top of the frame with a pair of clamps. The polyethylene was then stretched across the various horizontal support beams along the entire length of the frame. The first horizontal support beam was located 0.34 meters from the top edge of the frame. The first chamber stretched from the top edge of the frame to the first horizontal support at an inclined angle of 51°. After stretching over the first horizontal support the polyethylene continued straight down the length of the frame for 0.34 meters at an angle of zero degrees from the vertical. The polyethylene then stretched across a third horizontal support beam and angled inward at 51°, in the reverse direction of the first angled section. The polyethylene then continued down the opposite length of the frame vertically at an angle of zero degrees from the vertical for a length of 0.34 meters. The polyethylene then stretched across another support beam and angled back in the forward direction at an angle of 51° and then was anchored to a reservoir tank with another pair of clamps.

*B. braunii* was cultured indoors in the reactor in a modified Chu 13 media (Example 1) using fluorescent lights at an irradiation of 150-250 µmol/m$^2$s on a 12 hour light illumination cycle. The indoor setting and the consistent artificial light allowed many parameters of the reactor to be adjusted in order to validate the design and refine the construction of the reactor. The temperature inside the workshop where the test reactor was located was held at a temperature between 24° C. and 28° C. The reactor was inoculated with fresh *B. braunii* that had been cultured in the laboratory under similar conditions and had reached saturation. Once inoculated, the reactor was kept continuously running and samples were taken every 48 hours.

Table 3 summarizes the various adjustments that were made to the reactor during the experimental trials along with the algae growth properties that were evaluated for each configuration.

TABLE 3

Reactor configuration and resulting algae growth characteristics

| Test number | Reactor Configuration | Peak Biomass Density (g/L Dry Weight) | Specific Growth Rate |
|---|---|---|---|
| 1 | Initial (as described in text above) | 0.331 | 0.0573 |
| 2 | Same as test 1, volume reduced to 30 L | 0.398 | 0.059 |
| 3 | Width reduced to 0.19 m, vertical chambers shortened to 0.25 m, angled compartments reduced to 0.33 m, angle increased to 56°, extra angled and vertical compartment added, 70 L reactor volume | 0.746 | 0.073 |
| 4 | Same as test 3 with illumination on both faces of reactor | 1.273 | 0.118 |
| 5 | Same as test 4 with doubled inoculation | 1.315 | 0.175 |

The productivity of the initial configuration of the reactor (test 1) was adequate, but lower than what was expected and the specific growth rate was also lower than expected. It was demonstrated that the polyethylene material in the Accordion configuration was suitable for producing algae and could sustain stable production for several weeks. The initial configuration validated the suitability of the pumping system as well as the overall design of the system, e.g., algae cells were able to flow freely from one chamber to the next without accumulating in any one section. The culture volume also remained homogenous throughout the chambers as well as the reservoir tank. A reduced culture volume (test 2) increased biomass production slightly.

One observation of the initial rector configuration was that each chamber remained only partially filled with fluid, regardless of the inlet flow rate to the top reactor chamber. Thus, each chamber was reduced in size and two additional chambers were added (test 3) in order to maintain the same overall size of the reactor. The width of the reactor was reduced to 0.19 m, resulting in angled chambers of 0.33 m in length that were inclined at 56°. The horizontal support beams were repositioned closer together, resulting in vertical chambers that were 0.25 m in length. The reactor volume was 70 L and recirculated at a flow rate of 28 L/min.

A significant increase in biomass productivity and a higher growth rate was observed in the re-configured bioreactor. This suggested that the illuminated surface area of the reactor was being used more effectively and that a higher photosynthetic efficiency was being realized. The major difference between the first and second configurations was the surface area that was made available to the algae for photosynthesis. The volumes and the flow rates were identical between both the initial and reconfigured case. The reconfigured case allowed for algae to more fully occupy the illuminated surface area of each chamber and the addition of two extra chambers provided for even more surface area all while maintaining the same overall frame height.

One aspect of the bioreactor that was considered was the fact that the vertical chambers alternated from one face of the frame to the other. This is significant because the fluorescent lights that provided illumination were located on only one side of the reactor. Subsequently, any vertical chamber that was located on the face of the reactor that was on the opposite side of the lights received significantly less illumination than a vertical chamber located on the face of the reactor close to the fluorescent lights. This configuration represents a situation that is less than optimal and does not adequately simulate the conditions that might occur in an outdoor or natural light setting. The vertical chambers closest to the fluorescent lights received 250 µmol/m²s, while the vertical chambers on the opposite face received less than 100 µmol/m²s. In a setting where the reactor would be under natural illumination the difference between a vertical chamber that was 0.18 m either farther or closer to the sun would be insignificant, however, this distance is quite significant when artificial illumination is being used. In order to address this, a bank of fluorescent lights was placed alongside both faces of the reactor (test 4) in order to more evenly distribute the illumination over the entire reactor. When the previous reactor configuration was operated with a light bank on each side the peak biomass density increased to 1.273 g/L on a dry weight basis and the specific growth rate increased to 0.118 $d^{-1}$.

Another observation that was made was that the bioreactor showed a longer lag phase than algae cultures that were grown in laboratory. In an effort to reduce the length of the lag phase the inoculation for the reactor at the start of experiments was doubled (test 5). Maintaining the previously evaluated reactor configuration, with light banks on each face, the doubled inoculation resulted in an increased peak algae biomass density of 1.315 g/L and an increased specific growth rate of 0.175 $d^{-1}$. After making all of the above adjustments to the bioreactor, the resulting biomass productivity was more in line with algae cultures that were grown in the laboratory and with reported values in the literature that were grown under similar conditions.

Example 4

Comparison of ACCORDION Photobioreactor Conditions

This example describes comparisons of different ACCORDION photobioreactor conditions for algae growth.

Three different parameters of the ACCORDION photobioreactor system were varied during algal culture. The ACCORDION photobioreactors were housed in a greenhouse in Tucson, Ariz. The experiments described in this example were carried out during a period from July to October. As a control, a 1 liter flask was kept stirred in the greenhouse. The greenhouse temperature was regulated to be approximately 78° F. during the day and approximately 69° F. during the night (±3° F.). The parameters were flow rate (14 L/min (low flow), 28 L/min (medium flow), and 42 L/min (high flow)), chamber angle (45° and 65° incline), and compartment openings (one opening per compartment, about 5 cm wide, serpentine layout or two openings per compartment, about 2.5 cm width per opening, alternating middle and edge positions; e.g., FIGS. 5A and 5B). Flow rate was regulated by including one, two, or three pumps, with each pump providing about 14 L/minute flow. The culture condition combinations are shown in Table 4. All configurations had a 60 liter system volume. Samples of algae culture (50 mL) were collected every 48 hours.

TABLE 4

ACCORDION photobioreactor parameter combinations

| Condition | Parameters |
|---|---|
| A1 | High flow, 45° incline, 1 opening |
| A2 | Medium flow, 45° incline, 1 opening |
| A3 | Low flow, 45° incline, 1 opening |
| B1 | Medium flow, 65° incline, 1 opening |
| B2 | Medium flow, 65° incline, 2 openings |
| B3 | Low flow, 65° incline, 1 opening |
| B4 | Low flow, 65° incline, 2 openings |
| B5 | High flow, 65° incline, 2 openings |
| C1 | Low flow, 45° incline, 2 openings |
| C2 | Medium flow, 45° incline, 1 opening |
| C3 | Medium flow, 45° incline, 2 openings |
| C4 | Low flow, 45° incline, 2 openings |
| C5 | High flow, 45° incline, 1 opening |

Figure 9:
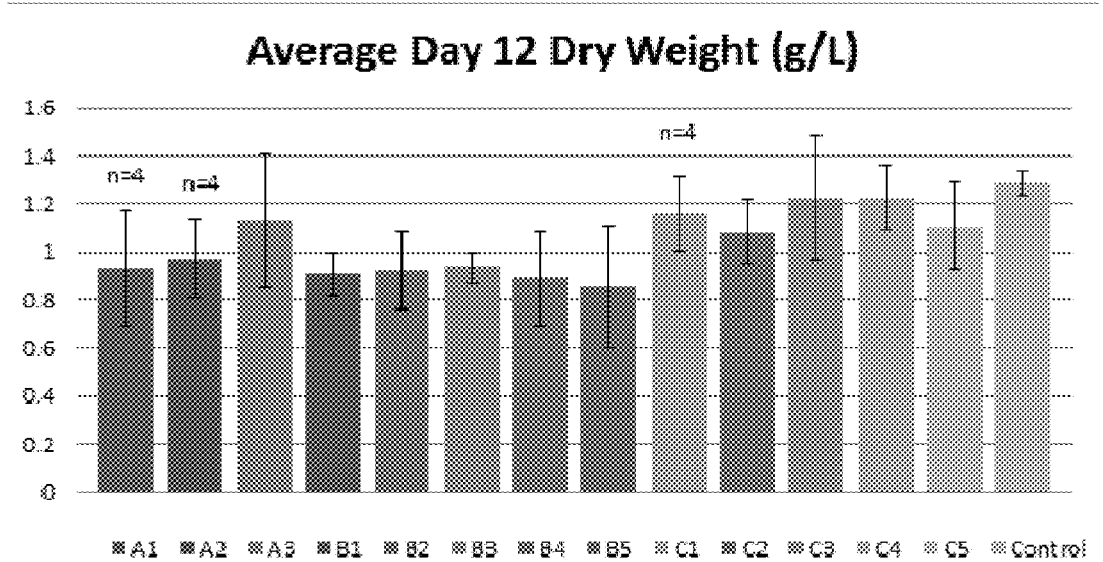
FIG. 9 is a bar graph showing average dry weight (g/L) on day 12 of culture in ACCORDION bioreactors with the conditions set forth in Table 4 and a control culture (stirred flask in greenhouse).

Algae growth under each set of conditions was determined by measuring dry weight (g/L) of the harvested algae. Growth curves from two independent experiments are shown in FIG. 8. The specific growth rate of each culture is shown in Table 5. Conditions C3 (medium flow, 45° incline, 2 openings) and C4 (low flow, 45° incline, 2 openings) showed the highest growth rate and average dry weight on day 12 of culture among the treatment conditions (Table 6; FIG. 8). The amount of algae (dry weight) produced by C3 and C4 was statistically indistinguishable from that produced in the control culture flask. Conditions A3, C1, C2, and C5 also produced statistically similar amounts of algae on day 12 of culture (Table 6; FIG. 9). The standard deviation of the day 12 dry weight for each treatment was calculated, n=3 for all treatments except A1, A2, and C1, for which n=4. The rank of each treatment condition for two experiments is shown in Table 7.

TABLE 5

Specific growth rate of algae in ACCORDION photobioreactor.

| Condition | Experiment 1 | Experiment 2 |
|---|---|---|
| B1 | 0.169179 | 0.180735391 |
| B2 | 0.153208 | 0.174155737 |
| B3 | 0.178405 | 0.186275015 |
| B4 | 0.168754 | 0.195286747 |
| B5 | 0.158379 | 0.193489203 |
| C1 | 0.195702 | 0.175351545 |
| C2 | 0.187844 | 0.173616001 |
| C3 | 0.203511 | 0.177062762 |
| C4 | 0.204857 | 0.191789595 |
| C5 | 0.206093 | 0.186705534 |
| A1 | 0.132646 | 0.150061738 |
| A2 | 0.171444 | 0.159539957 |
| A3 | 0.151147 | 0.181725982 |

TABLE 6

Algae dry weight on day 12 by condition

| Condition | Average day 12 dry weight | Standard Deviation |
|---|---|---|
| A1 | 0.929302 | 0.242644013 |
| A2 | 0.973225 | 0.166848841 |
| A3 | 1.1325 | 0.116672619 |
| B1 | 0.907196 | 0.088817745 |
| B2 | 0.924421 | 0.163453648 |
| B3 | 0.935843 | 0.062447333 |
| B4 | 0.889567 | 0.198602039 |
| B5 | 0.857072 | 0.251628342 |
| C1 | 1.161612 | 0.153271158 |
| C2 | 1.084343 | 0.130592423 |
| C3 | 1.225773 | 0.17786993 |
| C4 | 1.225921 | 0.135653446 |
| C5 | 1.106091 | 0.181147389 |

TABLE 7

Treatment rank

| Condition | Experiment 1 | Experiment 2 |
|---|---|---|
| A1 | 13 | 13 |
| A2 | 12 | 10 |
| A3 | 3 | 5 |
| B1 | 10 | 8 |
| B2 | 4 | 9 |
| B3 | 8 | 7 |
| B4 | 6 | 11 |
| B5 | 5 | 12 |
| C1 | 11 | 4 |
| C2 | 7 | 6 |
| C3 | 2 | 1 |
| C4 | 1 | 2 |
| C5 | 9 | 3 |

Treatment rank is shown as 1 = highest dry weight; 13 = lowest dry weight

Example 5

Measuring Hydrodynamic Parameters

The residence time distribution (RTD) of a reactor is a probability function that describes the amount of time that a single fluid element spends inside of the reactor. Residence time distribution experiments provide the basis for evaluating the fluid dynamics and the subsequent mixing conditions that occur in a particular reactor configuration. In particular, a tracer experiment provides a reliable and straightforward method for determining dimensionless quantities such as the vessel dispersion number, the Bodenstein Number, and the Reynolds Number. The vessel dispersion number is defined below.

$$\frac{D}{uL}$$

where D is the axial dispersion coefficient, u is the liquid flow velocity in meters per second, and L is the length of the reactor that the fluid passes through. The axial dispersion coefficient, D, is a representation of the degree of back mixing that occurs as fluid flows through the reactor. When the vessel dispersion number approaches zero the fluid can be characterized as plug flow. In a plug flow scenario there is assumed to be no mixing along the axial direction of the reactor, in other words, fluid moves through the reactor in a discrete "plug" that does not mix or interact with either the "plug" in front or behind it inside the reactor. In an ideally mixed flow scenario it is assumed that all fluid entering the reactor is instantly and completely mixed into the bulk flow of the reactor. It is assumed that there is no variation within the bulk flow and that all fluid elements contained within the bulk are identical. A reactor behaving in plug flow fashion will have a residence time distribution function that resembles a dirac delta function at the average residence time. A reactor behaving in an ideally mixed manner will have a residence time distribution function that approximates an exponential decay function.

The reciprocal of the vessel dispersion number is the Bodenstein number; a Bodenstein number of less than 0.1 indicates ideally mixed flow while a Bodenstein number of greater than 20 indicates plug flow conditions. The Bodenstein number is given below, $$Bo = \frac{uL}{D}$$

The Reynolds number is the ratio of viscous forces to inertial forces that occur during fluid flow. The value of the Reynolds number determines whether or not the fluid is experiencing laminar or turbulent flow conditions. Not only does the value of the Reynolds number give an indication to the degree of mixing that is taking place within the reactor, it also provides an important basis for determining if two flows are similar or not. The Reynolds number is given below:

$$Re = \frac{u\rho d}{\mu}$$

where u is the fluid velocity, $\rho$ is the fluid density, d is the characteristic diameter of the reactor, and $\mu$ is the fluid viscosity.

The average residence time can be determined experimentally by evaluating the residence time distribution, which can be constructed from experimentally determined concentration versus time data. In order to obtain a concentration versus time curve a tracer experiment is performed. A pulse of a tracer fluid (such as NaCl) is introduced into the fluid volume at the inlet of the reactor. The concentration of that pulse in the fluid exiting the reactor is then measured as time passes. A suitable tracer must be non-reactive and should not alter the physical properties of the reactor; such as viscosity and density. It is also assumed that the reactor is a steady state and the fluid inside the reactor is incompressible.

In the case of a reactor with a small extent of dispersion, the RTD curve is represented by the equation:

$$C_\theta = \frac{1}{2\left(\pi\left(\frac{D}{uL}\right)\right)^{\frac{1}{2}}} \exp\left[-\frac{(1-\theta)^2}{4\left(\frac{D}{uL}\right)}\right]$$

$C_{74}$ is the normalized concentration, $\theta$ is the normalized time and $$\frac{D}{uL}$$

is the vessel dispersion number. Normalized time is defined as t divided by the average residence time*.

t* is the average residence time and is defined as:

$$t^* = \frac{\int_0^\infty tC dt}{\int_0^\infty C dt}$$

and approximated as:

$$t^* = \frac{\sum tC\Delta t}{\sum C\Delta t}$$

The variance of the RTD, and in fact the variance of any distribution, is a measure of how far a value lies from the mean. Thus, the normalized variance of RTD is proportional to the vessel dispersion number:

$$\sigma_\theta^2 = \frac{\sigma^2}{t^{*2}} = 2\left(\frac{D}{uL}\right)$$

The variance is defined as:

$$\sigma^2 = \frac{\int_0^\infty (t-t^*)^2 C dt}{\int_0^\infty C dt} = \frac{\int_0^\infty t^2 C dt}{\int_0^\infty C dt} - t^{*2}$$

and can be approximated as the following:

$$\sigma^2 \cong \frac{\sum (t-t^*)^2 C\Delta t}{\sum C\Delta t} = \frac{\sum t^2 C\Delta t}{\sum C\Delta t} - t^{*2}$$

The vessel dispersion number can now be determined from experimental concentration data that is obtained from tracer experiments.

The equations listed above are valid for small extents of dispersion, meaning a value of $$\frac{D}{uL}$$

that is less than 0.01. When $$\frac{D}{uL}$$

is less than 0.01 the error involved in determining the vessel dispersion number is less than 5%. For dispersion numbers greater than 0.01 the following equation is used for evaluating reactors with large extents of dispersion.

$$\sigma_\theta^2 = \frac{\sigma^2}{t^{*2}} = 2\frac{D}{uL} - 2\left(\frac{D}{uL}\right)^2(1-e^{\frac{-uL}{D}})$$

Example 6

Residence Time Distribution

This example describes experiments to determine residence time distribution for various ACCORDION bioreactor configurations.

Residence time distribution experiments were performed for the initial reactor configuration as well as the reconfigured reactor described in Example 3. The initial configuration (test 1; Table 3) was tested with a reactor volume of 70 L and a flow rate of 28 L/min. In order to carry out the residence time distribution experiments the reactor was operated in an open arrangement with none of the effluent being returned to the reactor. Two reservoir tanks were used for this particular arrangement, one tank of fresh DI water for the reactor inlet, and a second for the effluent from the reactor. As the fluid passed through the reactor and exited it was directed to a drain and not returned to the reactor. A continuous supply of DI water was instead supplied to the reactor inlet. This configuration represented an "open" configuration opposed to the "closed" configuration that is indicative of the normal reactor operating conditions. The NaCl tracer was instantaneously added to the first inlet tank and the measurements were taken at the outlet of the reactor. In all cases, a 100 g/L NaCl impulse equal to one percent of the total reactor volume was instantaneously added at the reactor inlet. The concentration of the tracer within the rector was measured as time passed by using a Hanna Instruments electrical conductivity probe. The probe was connected to a Campbell Scientific CR 800 series data logger. Electrical conductivity readings were recorded by the data logger at one second intervals. Prior to the addition of the tracer pulse the electrical conductivity was measured until a suitable baseline reading was observed. Measurements were taken until the conductivity readings returned to within 3% of the baseline. The electrical conductivity readings were correlated to NaCl concentration by using a standard curve that was developed in the laboratory.

Figure 10A:
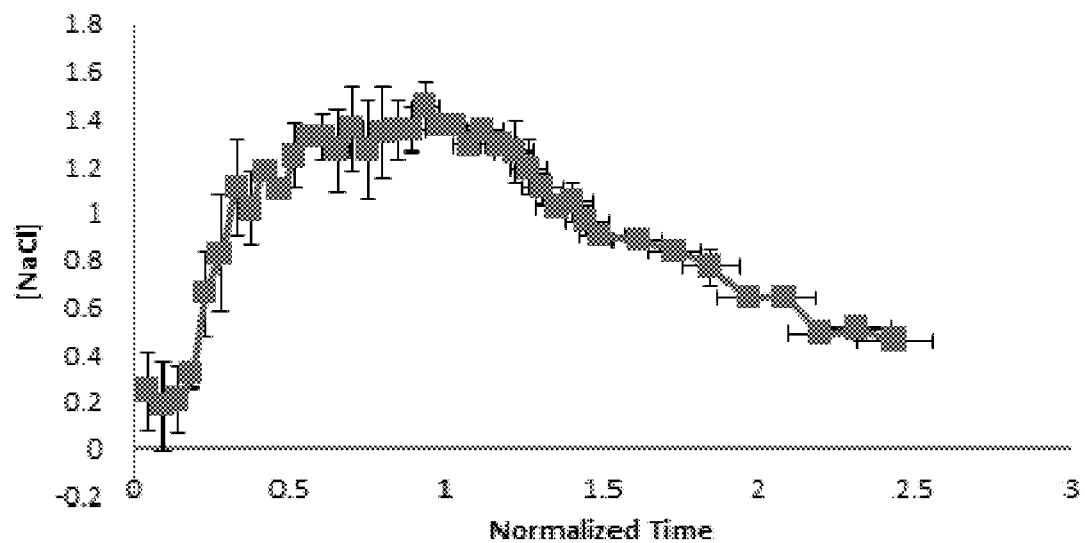
FIGS. 10A and 10B are a pair of graphs showing residence time distribution for two different ACCORDION bioreactor configurations, initial (FIG. 10A) and reconfigured (FIG. 10B), as described in Example 3.

Based on the tracer experiments, the average residence time obtained for the initial reactor configuration was 42 seconds (FIG. 10A). This means that on average, a typical algal cell spent 42 seconds inside the reactor chambers. Based on the data from the residence time distribution experiments, the vessel dispersion number was found to 0.146 and the Bodenstein number was 7.5. The Reynolds number for the flow conditions that were being evaluated was 451.

Figure 10B:
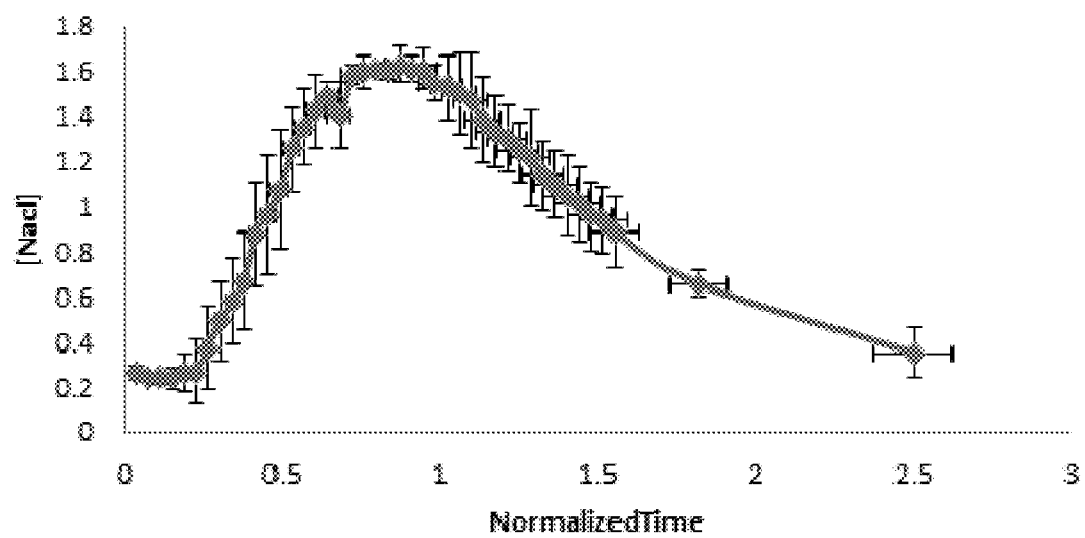

Tracer experiments conducted on the reconfigured reactor (test 4; Table 3) showed an average residence time of 132 seconds, a vessel dispersion number of 0.239, and a Bodenstein number of 4.1 (FIG. 10B). The Reynolds number for the given flow conditions was 900. The Bodenstein number of 4.1 was lower than the initially configured reactor and comes closer to approaching the case of ideal mixing. The shape of the distribution resembles an exponential decay curve, indicating that there was at least a moderate degree of mixing taking place in the reactor. In both configurations the residence time distribution indicated that the reactor was behaving more as an ideally mixed system than a plug flow system. Comparatively, the reconfigured reactor exhibited a Bodenstein number that was 42% smaller than the initial configuration. This suggested that there was a greater degree of mixing taking place in the reconfigured system and that the reconfigured reactor behaved in more of an ideally mixed manner than the initial case.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A bioreactor comprising:
   (a) a first sheet and a second sheet, wherein the second sheet is disposed adjacent to the first sheet and the first and second sheets are sealed along a first longitudinal edge, a second longitudinal edge, a first horizontal edge, and a second horizontal edge, and comprising at least one intermediate horizontal seal between the first horizontal edge and the second horizontal edge, thereby forming at least two chambers for holding fluid in series along a vertical axis, wherein each of the two or more chambers is oriented at an angle relative to the vertical axis, wherein the angle is about 0° to about 90° and at least one of the chambers is oriented at an angle greater than 0° and at least one of the chambers is oriented at an angle of about 0° relative to the vertical axis, wherein the at least two chambers alternate between a chamber oriented at an angle greater than 0° and a chamber oriented at an angle of about 0° relative to the vertical axis, and wherein there is at least one opening in each of the first horizontal edge, the second horizontal edge, and the at least one intermediate horizontal seal;
   (b) a support structure comprising at least one horizontal support, wherein the horizontal support is located at or near the position of the intermediate horizontal seal;
   (c) a reservoir below the second horizontal edge of the first and second sheets; and
   (d) means for pumping fluid from the reservoir to the first horizontal edge of the first and second sheets.

2. The bioreactor of claim 1, wherein at least one of the first and second sheets is transparent.

3. The bioreactor of claim 1, wherein the first and second sheets each comprise a flexible material.

4. The bioreactor of claim 3, wherein the flexible material is selected from polyethylene and polyvinyl chloride.

5. The bioreactor of claim 1, wherein the angle greater than 0° relative to the vertical axis is about 30° to about 75°.

6. The bioreactor of claim 5, wherein the angle greater than 0° relative to the vertical axis is about 45° to about 65°.

7. The bioreactor of claim 1, wherein the openings in each of the first horizontal edge, intermediate horizontal seal, and second horizontal edge are not aligned in the vertical axis.

8. The bioreactor of claim 7, wherein the openings alternate between a location adjacent to the first longitudinal edge and a location adjacent to the second longitudinal edge.

9. The bioreactor of claim 7, wherein the openings alternate between at least one location adjacent to the first longitudinal edge and/or the second longitudinal edge and a location substantially in the center of the intermediate horizontal seal.

10. The bioreactor of claim 1, comprising two or more intermediate horizontal seals between the first horizontal edge and the second horizontal edge.

11. The bioreactor of claim 10, comprising three to twenty intermediate horizontal seals.

12. The bioreactor of claim 1, further comprising at least one delivery device for providing gas and/or nutrients to fluid within the bioreactor.

13. The bioreactor of claim 12, wherein the delivery device provides gas and/or nutrients to fluid in the reservoir.

14. A method for culturing cells using the bioreactor of claim 1 comprising the step of: circulating a suspension of cells in a nutrient solution in the bioreactor.

15. The method of claim 14, wherein the cells comprise microalgae, macroalgae, bacteria, fungi, plant cells, or mammalian cells.

16. The method of claim 15, wherein the microalgae is *Chlamydomonas reinhardtii, Chlorella vulgaris, Spirulina platensis, Haematococcus pluvialis, Botryococcus braunii, Nannochloropsis occulata, Crypthecodinium cohnii*, or *Thraustochytrium roseum*.

17. The method of claim 14, wherein the suspension of cells is circulated at a flow rate of about 10-50 liters per minute.

18. The method of claim 17, wherein the flow rate is about 14-42 liters per minute.

19. The method of claim 14, wherein the bioreactor is exposed to a light source.

20. The method of claim 19, wherein the light source is sunlight.

21. The method of claim 19, wherein the orientation of one or more of the chambers relative to the vertical axis is at an angle that maximizes exposure of the one or more chambers to radiant energy from the light source.

22. The bioreactor of claim 1, wherein the at least one horizontal seal between the first horizontal edge and the second horizontal edge is formed by pressure from a horizontal support, by an adhesive, or by a heat seal.

* * * * *